(12) United States Patent
Labhasetwar et al.

(10) Patent No.: US 11,446,039 B2
(45) Date of Patent: *Sep. 20, 2022

(54) SURGICAL CLIP APPLIER

(71) Applicant: Cilag GmbH International, Zug (CH)

(72) Inventors: Disha V. Labhasetwar, Cincinnati, OH (US); Michael J. Stokes, Cincinnati, OH (US); Gregory G. Scott, Cincinnati, OH (US); Chester O. Baxter, III, Loveland, OH (US); Michael A. Murray, Bellevue, KY (US); Kevin A. Larson, Maineville, OH (US); Ryan J. Laurent, Loveland, OH (US)

(73) Assignee: Cilag GmbH International, Zug (CH)

( * ) Notice: Subject to any disclaimer, the term of this patent is extended or adjusted under 35 U.S.C. 154(b) by 272 days.

This patent is subject to a terminal disclaimer.

(21) Appl. No.: 16/806,865

(22) Filed: Mar. 2, 2020

(65) Prior Publication Data

US 2020/0214711 A1 Jul. 9, 2020

Related U.S. Application Data

(63) Continuation of application No. 15/674,166, filed on Aug. 10, 2017, now Pat. No. 10,617,429.

(51) Int. Cl.
*A61B 17/128* (2006.01)
*A61B 90/00* (2016.01)
*A61B 17/00* (2006.01)

(52) U.S. Cl.
CPC ........ *A61B 17/128* (2013.01); *A61B 17/1285* (2013.01); *A61B 2017/00367* (2013.01);
(Continued)

(58) Field of Classification Search
CPC .......................... A61B 17/128; A61B 17/1285
See application file for complete search history.

(56) References Cited

U.S. PATENT DOCUMENTS

| 5,171,249 A | 12/1992 | Stefanchik et al. |
| 5,409,498 A | 4/1995 | Braddock et al. |

(Continued)

FOREIGN PATENT DOCUMENTS

EP 2832254 A1 2/2015

OTHER PUBLICATIONS

U.S. Appl. No. 15/674,166, filed Aug. 10, 2017, Disha V. Labhasetwar et al.

(Continued)

*Primary Examiner* — Ryan J. Severson
(74) *Attorney, Agent, or Firm* — Mintz Levin Cohn Ferris Glovsky and Popeo, P.C.

(57) ABSTRACT

A surgical clip applier and methods for applying surgical clips to a vessel, duct, shunt, etc., during a surgical procedure are provided. In one exemplary embodiment, a surgical clip applier is provided having a housing with a trigger movably coupled thereto and a shaft extending therefrom with opposed jaws formed on a distal end thereof. The trigger is adapted to advance a clip to position the clip between the jaws, and to move the jaws from an open position to a closed position to crimp the clip positioned therebetween. The surgical clip applier can include a variety of features to facilitate use of the device, including features to prevent misalignment of the jaws and clip therebetween, features to protect the jaws, and features to ensure proper closure of the jaws and clip therebetween.

11 Claims, 20 Drawing Sheets

(52) U.S. Cl.
CPC ............... *A61B 2017/00477* (2013.01); *A61B 2017/00526* (2013.01); *A61B 2090/034* (2016.02); *A61B 2090/038* (2016.02)

(56) References Cited

U.S. PATENT DOCUMENTS

| | | |
|---|---|---|
| 5,431,668 A | 7/1995 | Burbank, III et al. |
| RE35,525 E | 6/1997 | Stefanchik et al. |
| RE38,445 E | 2/2004 | Pistl et al. |
| 8,353,897 B2 | 1/2013 | Doyle et al. |
| 8,465,501 B2 | 6/2013 | Matsuoka et al. |
| 8,920,438 B2 | 12/2014 | Aranyi et al. |
| 9,468,440 B2 | 10/2016 | Schulz et al. |
| 9,687,247 B2 | 6/2017 | Aranyi et al. |
| 9,763,668 B2 | 9/2017 | Whitfield et al. |
| 2006/0079115 A1 | 4/2006 | Aranyi et al. |
| 2010/0286670 A1 | 11/2010 | Doyle et al. |
| 2011/0245855 A1 | 10/2011 | Matsuoka et al. |
| 2014/0005696 A1 | 1/2014 | Schulz et al. |
| 2015/0080916 A1 | 3/2015 | Aranyi et al. |
| 2015/0190138 A1 | 7/2015 | Whitfield et al. |
| 2016/0213434 A1 | 7/2016 | Lohmeier et al. |
| 2017/0258472 A1 | 9/2017 | Aranyi et al. |
| 2019/0046196 A1 | 2/2019 | Stokes et al. |
| 2019/0046197 A1 | 2/2019 | Stokes et al. |
| 2019/0046198 A1 | 2/2019 | Stokes et al. |
| 2019/0046200 A1 | 2/2019 | Stokes et al. |
| 2019/0046201 A1 | 2/2019 | Labhasetwar et al. |
| 2019/0046206 A1 | 2/2019 | Stokes et al. |

OTHER PUBLICATIONS

International Search Report and Written Opinion for PCT/US2018/045552 dated Oct. 3, 2018 (9 pages).

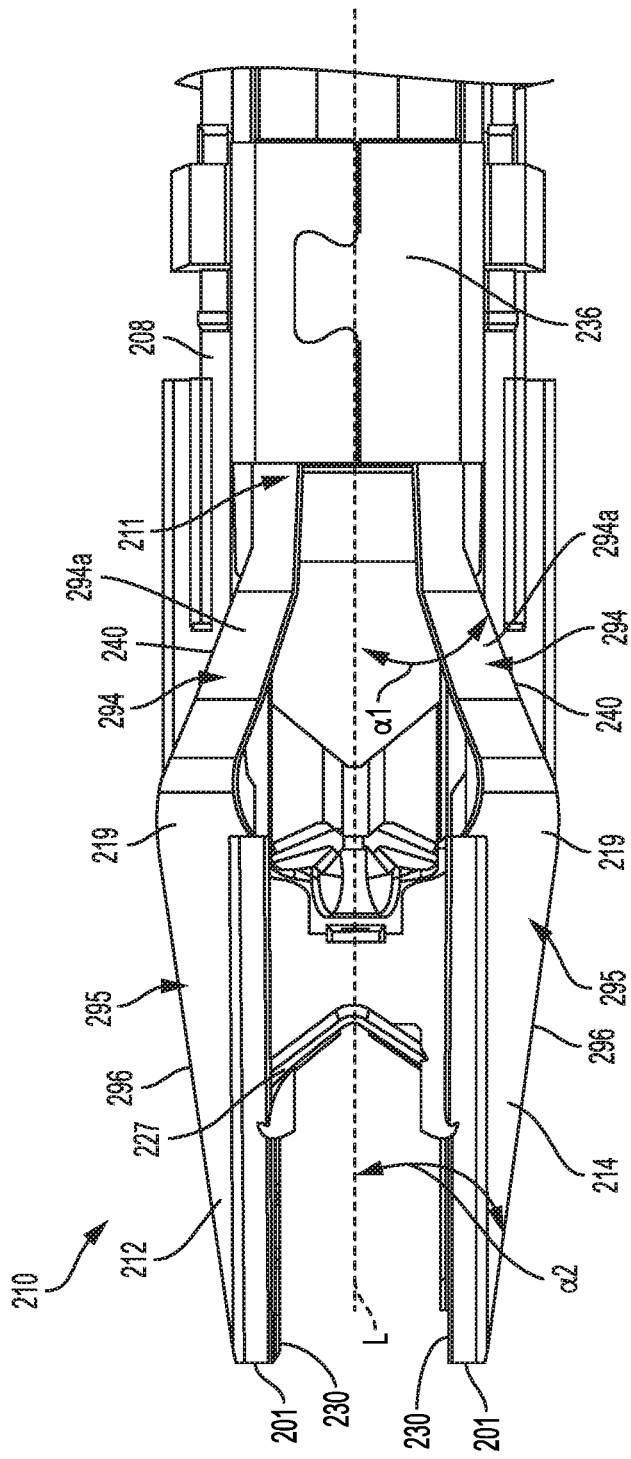

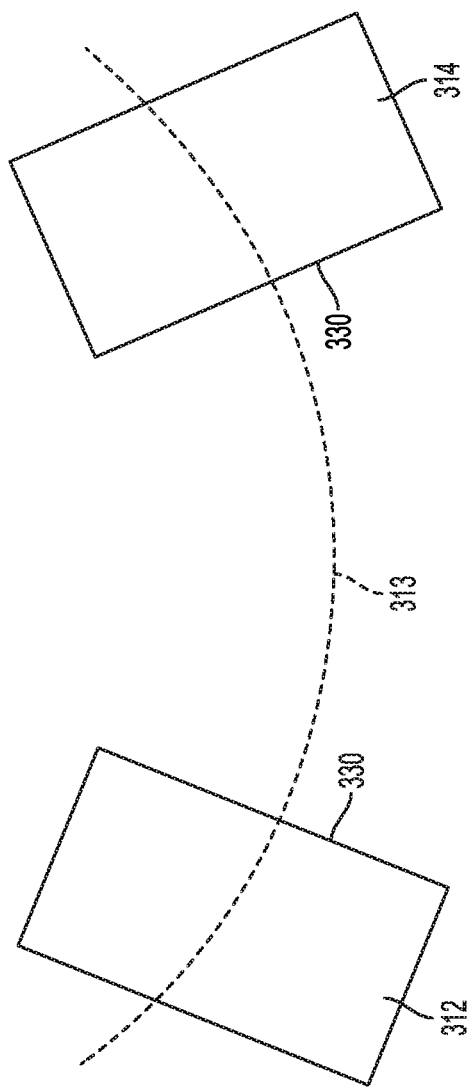

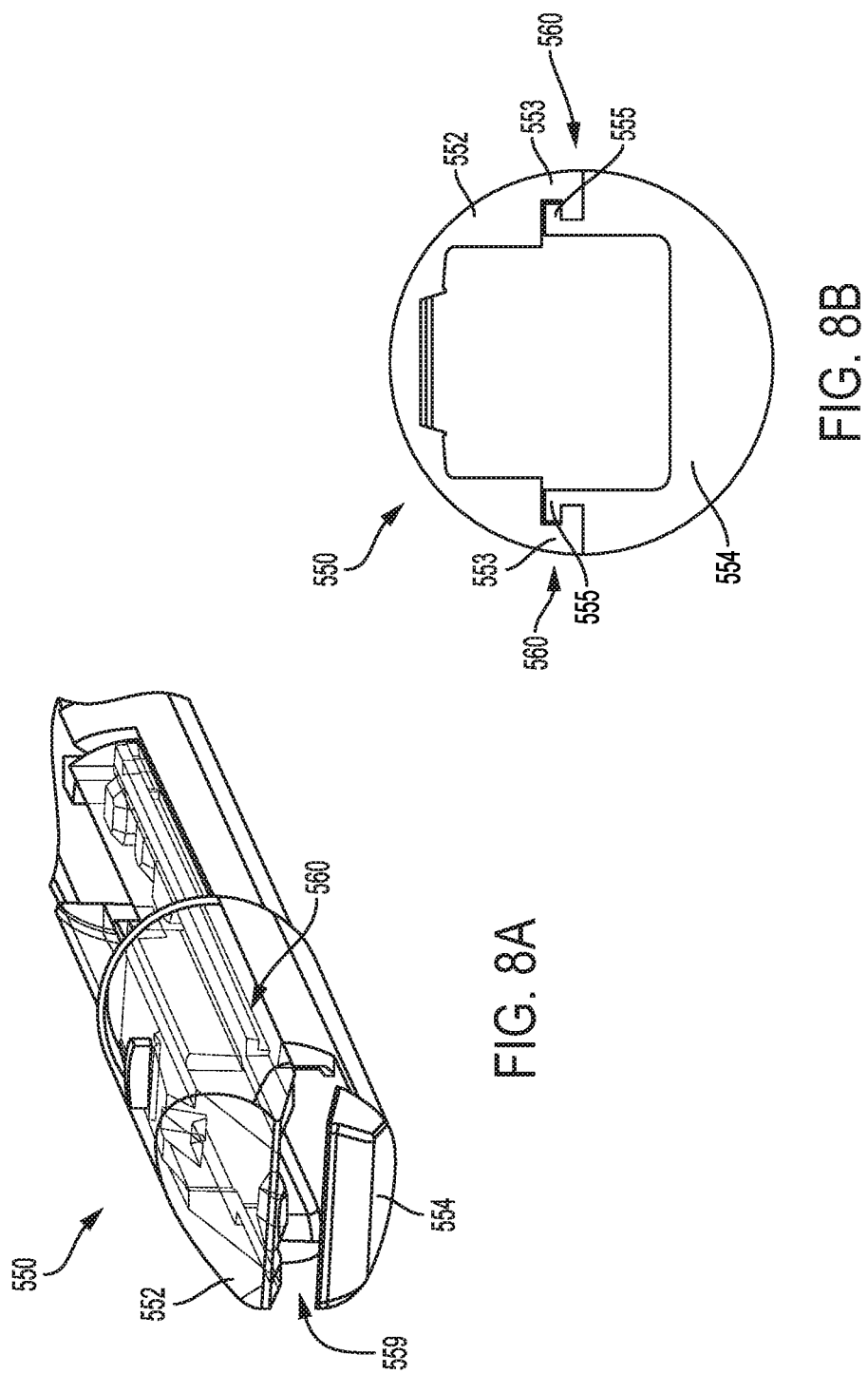

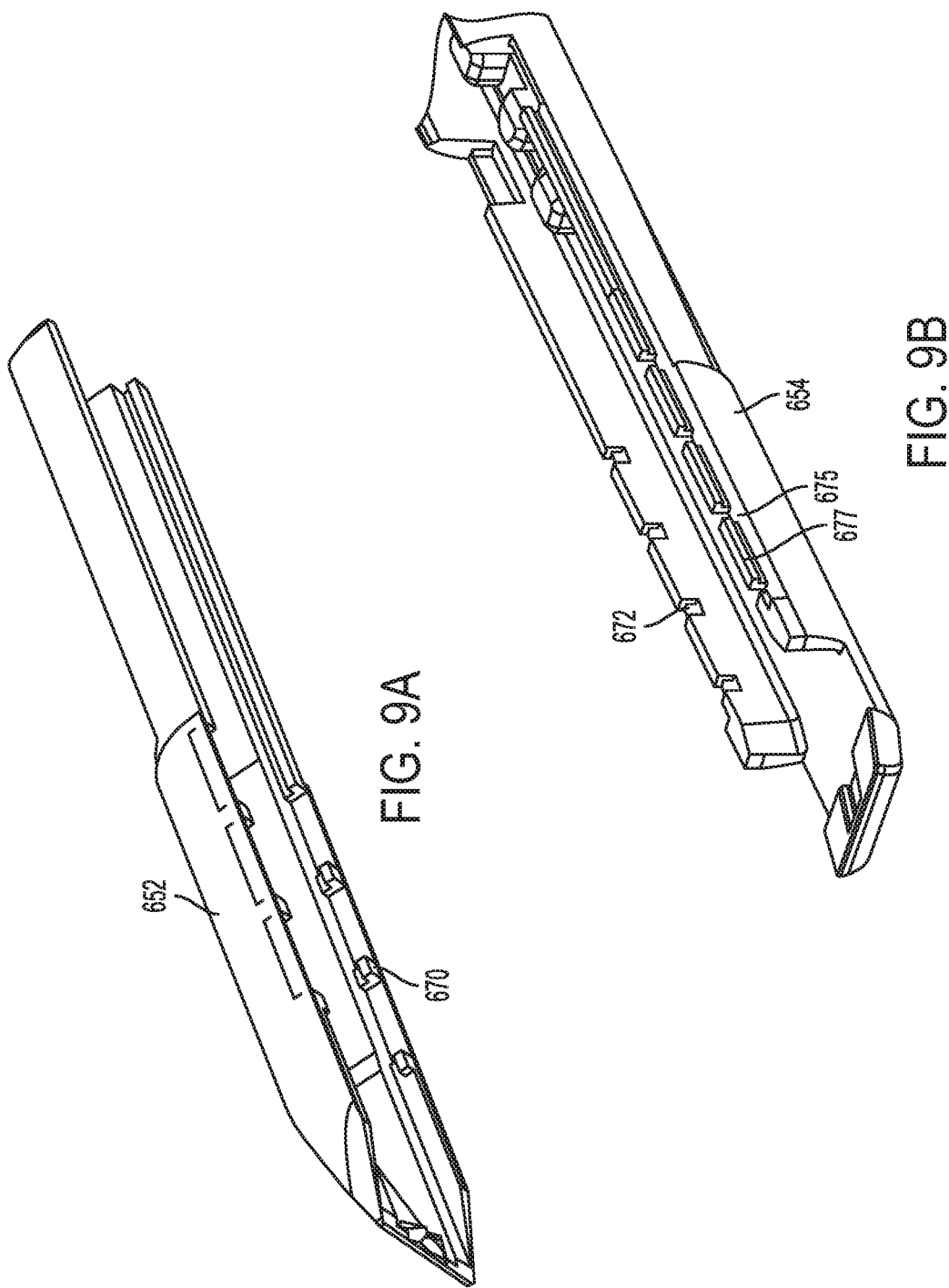

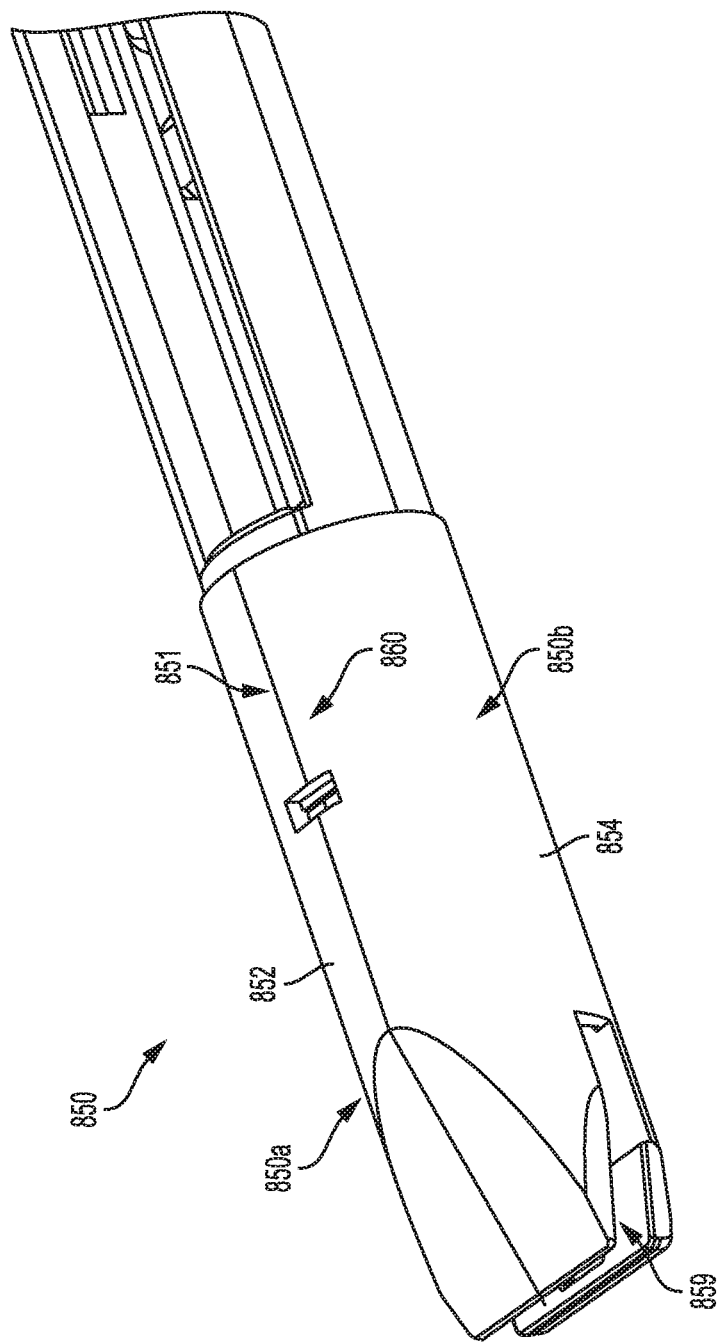

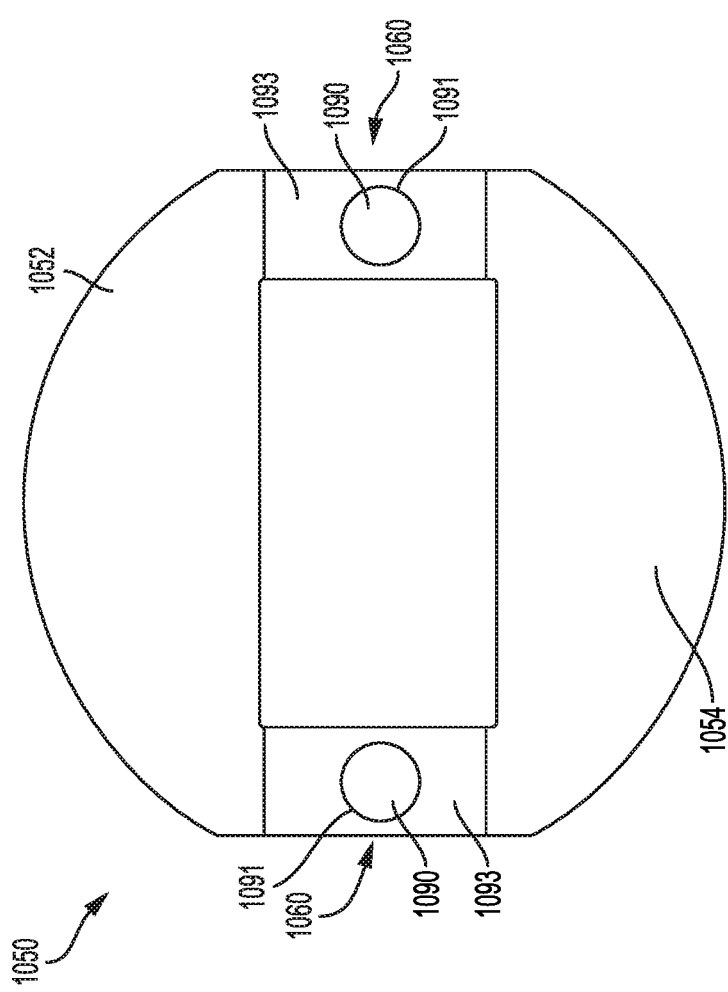

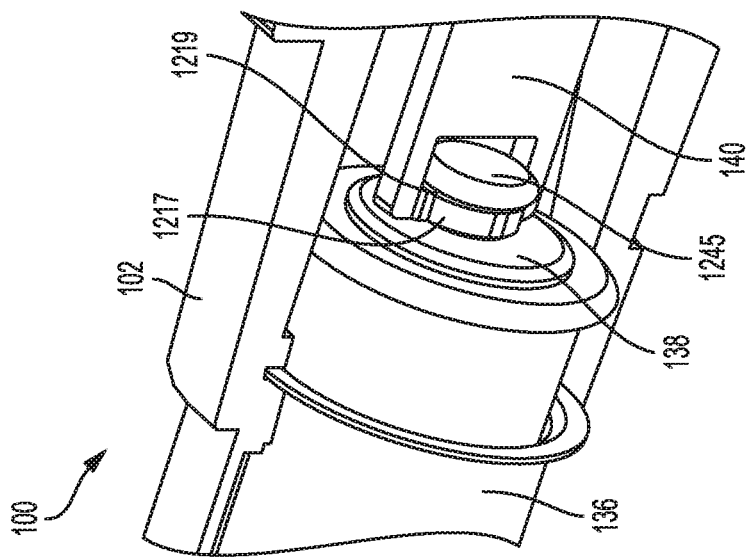
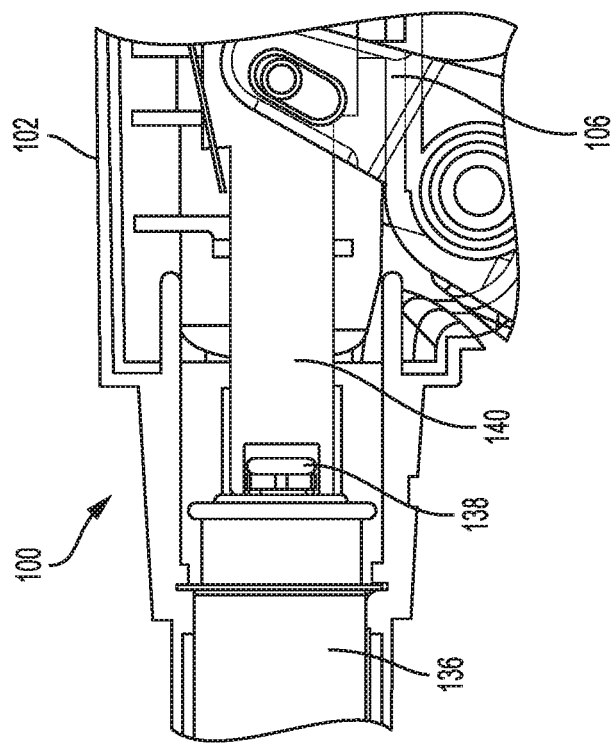
FIG. 14A
FIG. 14B

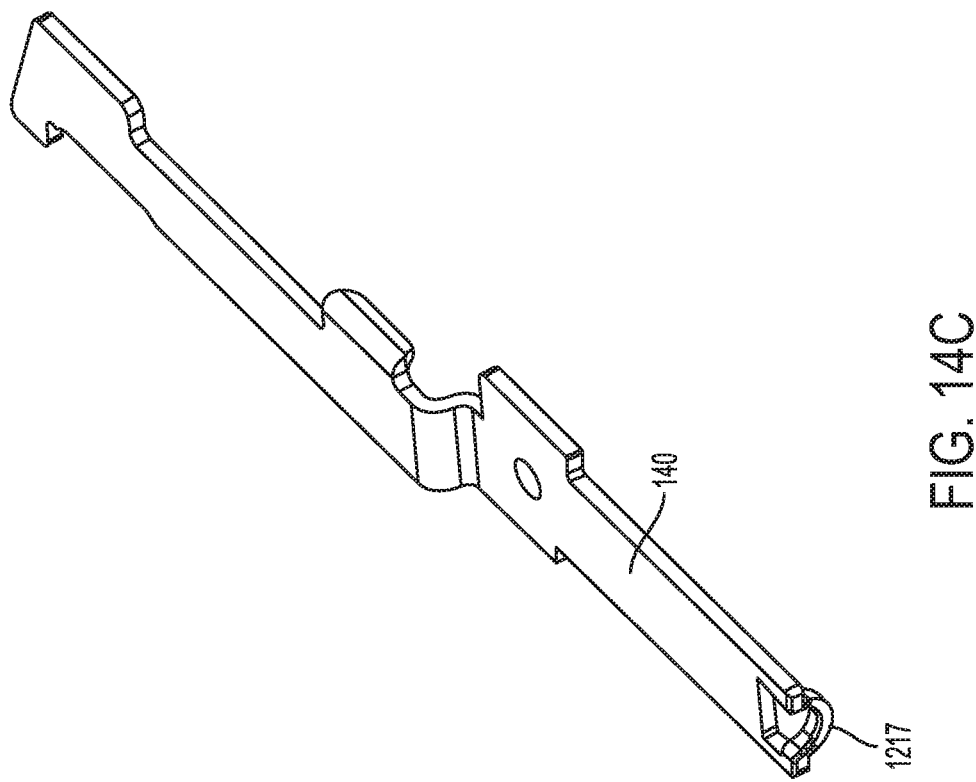

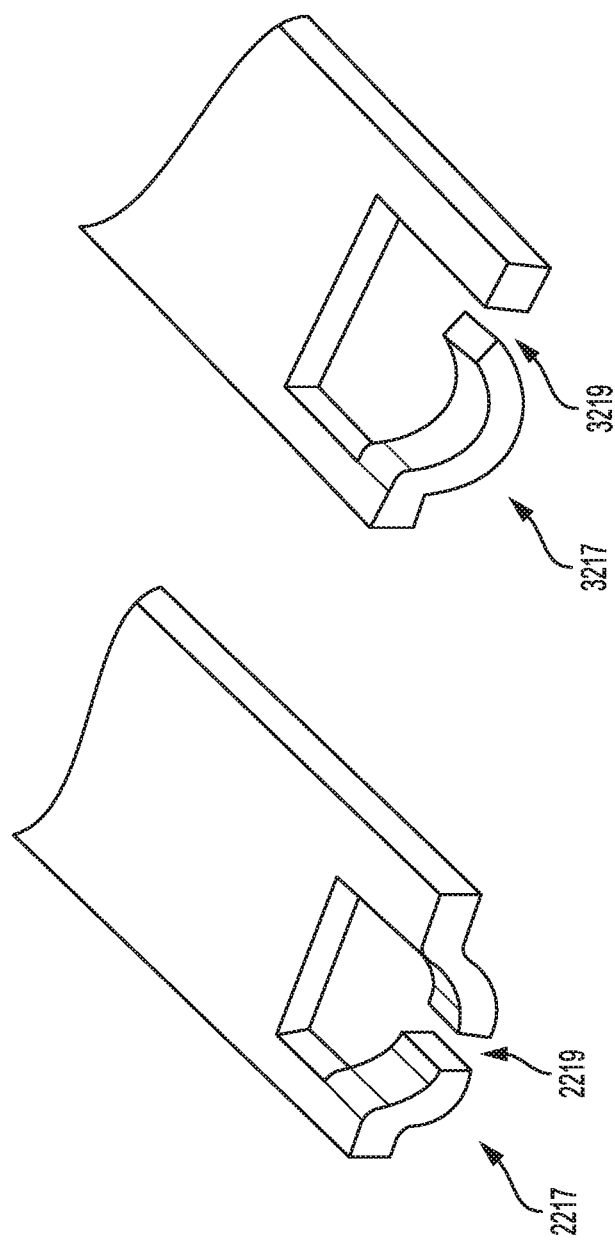

SURGICAL CLIP APPLIER

CROSS-REFERENCE TO RELATED APPLICATIONS

This application is a continuation of U.S. patent application Ser. No. 15/674,166 entitled "Surgical Clip Applier" filed Aug. 10, 2017, which is hereby incorporated by reference in its entirety.

FIELD

Surgical devices and methods are provided for applying surgical clips to ducts, vessels, shunts, etc.

BACKGROUND

In recent years surgery has markedly advanced through the performance of laparoscopic and endoscopic surgical procedures such as cholecystectomies, gastrostomies, appendectomies, and hernia repair. These procedures are accomplished through a trocar assembly, which is a surgical instrument used to puncture a body cavity. The trocar typically contains a sharpened obturator tip and a trocar tube or cannula. The trocar cannula is inserted into the skin to access the body cavity, by using the obturator tip to penetrate the skin. After penetration, the obturator is removed and the trocar cannula remains in the body. It is through this cannula that surgical instruments are placed.

One surgical instrument that is commonly used with a trocar cannula is a surgical clip applier for ligating a blood vessel, a duct, shunt, or a portion of body tissue during surgery. Most clip appliers typically have a handle with an elongate shaft having a pair of movable opposed jaws formed on an end thereof for holding and forming a ligation clip therebetween. The jaws are positioned around tissue, such as the vessel or duct, and the clip is crushed or formed on the tissue by the closing of the jaws.

Some drawbacks of current clip appliers include the jaws becoming misaligned or not sufficiently closing during use, which can damage the jaws or inappropriately form the resulting clip, create surgical errors, and/or prolong surgical procedures. Other issues with current clip appliers can include the jaws not closing with sufficient force to form a clip positioned between the jaws. In some current clip appliers, the jaws do not have sufficient strength to fully form a clip in thick tissue or the jaws can be too flexible thereby causing the jaws to deform and not function properly. In addition, the subsystems which drive the closure of the jaws may exert too little or too much axial stroke, thus leading to not fully formed clips, or over-stressed and damaged (yielded outward) jaws, respectively. Other issues, such as damage to the jaws before use (e.g., during shipping of the clip applier) have been experienced with some current clip appliers, which can prevent the jaws from functioning properly. Accordingly, there remains a need for improved methods and devices for applying surgical clips to vessels, ducts, shunts, etc.

SUMMARY

Various surgical instruments and methods are disclosed herein for applying a surgical clip to tissue, such as a vessel, duct, shunt, etc. In one embodiment, of a surgical clip applier can include a housing, a shaft extending from the housing, and a jaw insert having a proximal portion disposed within the elongate shaft and extending in a first plane containing a longitudinal axis of the shaft. The jaw insert can also include a distal portion having opposed first and second jaws extending in a second plane transverse to the first plane. Each jaw can have a distal portion that extends transverse to a proximal portion, and an intersection between the proximal and distal portions can define a maximum width of the first and second jaws. The first and second jaws can have opposed inward facing surfaces on distal portions that define a clip track for receiving a distal-most clip from a plurality of clips disposed within the shaft. The opposed inward facing surfaces can extend non-parallel to one another when the jaws are in an open position and can extend substantially parallel to one another when the jaws are in a closed position. The first and second jaws can further include outer contact surfaces on the proximal portion. The surgical clip applier can further include a former tube extending along the shaft and disposed around the jaw insert proximal of the first and second jaws. The former tube can be movable distally to engage the outer contact surfaces to cause the first and second jaws to pivot from the open position to the closed position for deforming a clip seated in the clip track. As the jaws move to the closed configuration, an initial point of contact can occur at a distal-most tip of the first and second jaws. The former tube can include a coupling feature at a proximal end thereof. The surgical clip applier can further include a shroud assembly having first and second shrouds disposed around the pair of jaws. The shroud assembly can form a gap that limits movement of the jaws along a single plane, and the first and second shrouds can form at least one mechanical interlock configured to fix a height of the gap. The surgical clip applier can further include a former plate disposed within the housing and having a u-shaped hook on a distal end positioned on one side of and in engagement with a flange on a proximal end of the coupling feature such that distal movement of the former plate causes corresponding distal movement of the former tube while allowing rotation of the shaft and the former tube relative to the housing and the former plate. Additionally, the surgical clip applier can include a protective cap formed from a rigid material and disposed over the first and second jaws, wherein the protective cap is releasably retained on the first and second jaws by at least one detent.

The surgical clip applier can vary in a number of ways. For example, the at least one mechanical interlock can include a first mechanical interlock and a second mechanical interlock. In some embodiments, the first mechanical interlock can include at least one of a keyed sliding-fit coupling, a stepped sliding-fit coupling, and a snap-fit coupling. As another example, the second mechanical interlock can include a welded coupling between the first and second shrouds. In some embodiments, the first mechanical interlock can be positioned along top and bottom sides of the shroud assembly. As another example, the at least one mechanical interlock can include a first mechanical interlock having a hooked coupling and a second mechanical interlock having a spring flange coupling. In some embodiments, the u-shaped hook can be configured to extend around a side of the flange that is opposite from a direction of offset of the former plate relative to a longitudinal axis of the coupling feature. As another example, the u-shaped hook can include a space therealong. In some embodiments, the protective cap can include a spring flange having a protrusion that engages the at least one detent.

In another embodiment, a surgical clip applier is provided that can include a shaft having first and second jaws at a distal end thereof. Each jaw can have a proximal portion and a distal portion that extends transverse to the proximal portion, and the distal portion of the first and second jaws can have opposed inward facing surfaces defining a clip track for receiving a distal-most clip from a plurality of clips disposed within the shaft. The proximal portion of the first and second jaws can have outer contact surfaces, and an intersection between the proximal and distal portion can define a maximum width of the first and second jaws. The surgical clip applier can further include a former member disposed proximal of the first and second jaws and movable distally to engage the outer contact surfaces to cause the first and second jaws to pivot from an open configuration to a closed configuration for deforming a clip seated in the clip track. In certain embodiments, an initial point of contact can occur at a distal-most tip of the first and second jaws as the jaws move to the closed configuration.

The surgical clip applier can vary in a number of ways. For example, the surgical clip applier can further include a shroud assembly including first and second shrouds disposed around the first and second jaws. In some embodiments, the shroud assembly can form a gap that limits movement of the first and second jaws along a single plane, and the first and second shrouds can form at least one mechanical interlock configured to fix a height of the gap. As another example, the at least one mechanical interlock can include a first mechanical interlock and a second mechanical interlock. In some embodiments, the first mechanical interlock can include at least one of a keyed sliding-fit coupling, a stepped sliding-fit coupling, and a snap-fit coupling. As another example, the second mechanical interlock can include a welded coupling between the first and second shrouds. In some embodiments, the first mechanical interlock can be positioned along top and bottom sides of the shroud assembly. As another example, the at least one mechanical interlock can include a first mechanical interlock having a hooked coupling and a second mechanical interlock having a spring flange coupling. In some embodiments, the surgical clip applier can further include a protective cap formed from a rigid material and disposed over the first and second jaws, and the protective cap can be releasably retained on the first and second jaws by at least one detent. In some embodiments, the former member can include a coupling feature at a proximal end thereof, and the surgical clip applier can further include a former plate having a u-shaped hook on a distal end positioned on one side of and in engagement with a flange on a proximal end of the coupling feature such that distal movement of the former plate can cause corresponding distal movement of the former member while allowing rotation of the shaft and the former member relative to the former plate.

Another embodiment of a surgical clip applier can include an elongate shaft and a jaw insert having a proximal portion disposed within the shaft and extending in a first plane containing a longitudinal axis of the shaft. The jaw insert can further include a distal portion having opposed first and second jaws that extend in a second plane transverse to the first plane. The first and second jaws can include opposed inner surfaces defining a clip track therebetween for receiving a distal-most clip from a plurality of clips disposed within the shaft. The surgical clip applier can further include a former member disposed around the jaw insert and movable distally to cause the first and second jaws to move from an open position to a closed position to deform a clip seated in the clip track. The opposed inner surfaces of the first and second jaws can extend non-parallel to one another when the jaws are in the open position and can extend substantially parallel to one another when the jaws are in the closed position.

Another embodiment of a surgical clip applier can include a housing, a shaft extending from the housing, and a pair of jaws having a proximal portion extending at least partially into the shaft and a distal portion with the pair of jaws defining a clip track therebetween for receiving a distal-most clip from a plurality of clips disposed within the shaft. The surgical clip applier can further include a shroud assembly including first and second shrouds disposed around the pair of jaws. The shroud assembly can form a gap that limits movement of the jaws along a single plane. The first and second shrouds can form at least one mechanical interlock configured to fix a height of the gap. In some embodiments, the at least one mechanical interlock can include a first mechanical interlock and a second mechanical interlock. The first mechanical interlock can include at least one of a keyed sliding-fit coupling, a stepped sliding-fit coupling, and a snap-fit coupling. The second mechanical interlock can include a welded coupling between the first and second shrouds. The first mechanical interlock can be positioned along top and bottom sides of the shroud assembly. The at least one mechanical interlock can include a first mechanical interlock having a hooked coupling and a second mechanical interlock having a spring flange coupling.

Another embodiment of a surgical clip applier can include a housing, a shaft extending from the housing, and first and second jaws formed on a distal end of the shaft. The first and second jaws can define a clip track therebetween for receiving a distal-most clip from a plurality of clips disposed within the shaft. The surgical clip applier can further include a former tube that extends along the shaft and is movable distally to move the first and second jaws from an open position to a closed position to deform a clip disposed in the clip track. The former tube can have a coupling feature at a proximal end thereof. The surgical clip applier can further include a former plate disposed within the housing and having a u-shaped hook on a distal end positioned on one side of and in engagement with a flange on a proximal end of the coupling feature such that distal movement of the former plate causes corresponding distal movement of the former tube while allowing rotation of the shaft and the former tube relative to the housing and the former plate.

Another embodiment of a surgical clip applier can include a housing and a shaft extending from the housing. An end effector including a pair of jaws can be formed on a distal end of the shaft, and the pair of jaws can define a clip track therebetween for receiving a distal-most clip from a plurality of clips disposed within the shaft. In one embodiment, the surgical clip applier assembly can include a protective cap formed from a rigid material and disposed over the pair of jaws. The protective cap and the end effector can include at least one protrusion and the other one of the protective cap and the end effector can include at least one corresponding detent. The at least one protrusion can engage the at least one corresponding detent to retain the cap on the end effector. In some embodiments, the end effector can include a shroud assembly disposed around the pair of jaws.

BRIEF DESCRIPTION OF THE DRAWINGS

The invention will be more fully understood from the following detailed description taken in conjunction with the accompanying drawings, in which:

FIG. 5 is a bottom view of an embodiment of a pair of jaws;

FIG. 6 is a cross-sectional view of an embodiment of a pair of jaws showing a pathway of movement;

FIG. 8A is a side perspective view of yet another embodiment of a shroud showing a mechanical interlock formed between upper and lower shrouds, with the upper shroud being slidably engaged with the lower shroud;

FIG. 8B is a cross-sectional view of the shroud of FIG. 8A showing the mechanical interlock including a pair of first keyed tracks along the upper shroud that are slidably engaged with a pair of second keyed tracks along the lower shroud;

FIG. 9A is a bottom perspective view of an upper shroud of yet another embodiment of a shroud assembly;

FIG. 9B is a top perspective view of a lower shroud that couples to the upper shroud of FIG. 9A for forming the shroud assembly;

FIG. 11 is a top perspective view of yet another embodiment of a mechanical interlock formed between first and second sides of a shroud assembly;

FIG. 13 is a cross-sectional view of yet another embodiment of a mechanical interlock formed between upper and lower shrouds, the mechanical interlock including a reinforcement structure that extends along a reinforcement pathway extending through a coupling between the upper and lower shrouds;

FIG. 14A is a partial side view of the clip applier of FIGS. 1-4B showing a clip forming assembly that includes a former plate extending through the housing of the clip applier;

FIG. 14B is a partial side perspective view of the clip applier of FIG. 14A showing the former plate having a hook feature engaged with an inner coupling.

FIG. 14C is a top perspective view of the former plate of FIG. 14A showing the hook feature.

FIG. 14D is a partial top perspective view of another embodiment of the hook feature;

FIG. 14E is a partial top perspective view of yet another embodiment of the hook feature;

DETAILED DESCRIPTION OF THE INVENTION

Figure 1:
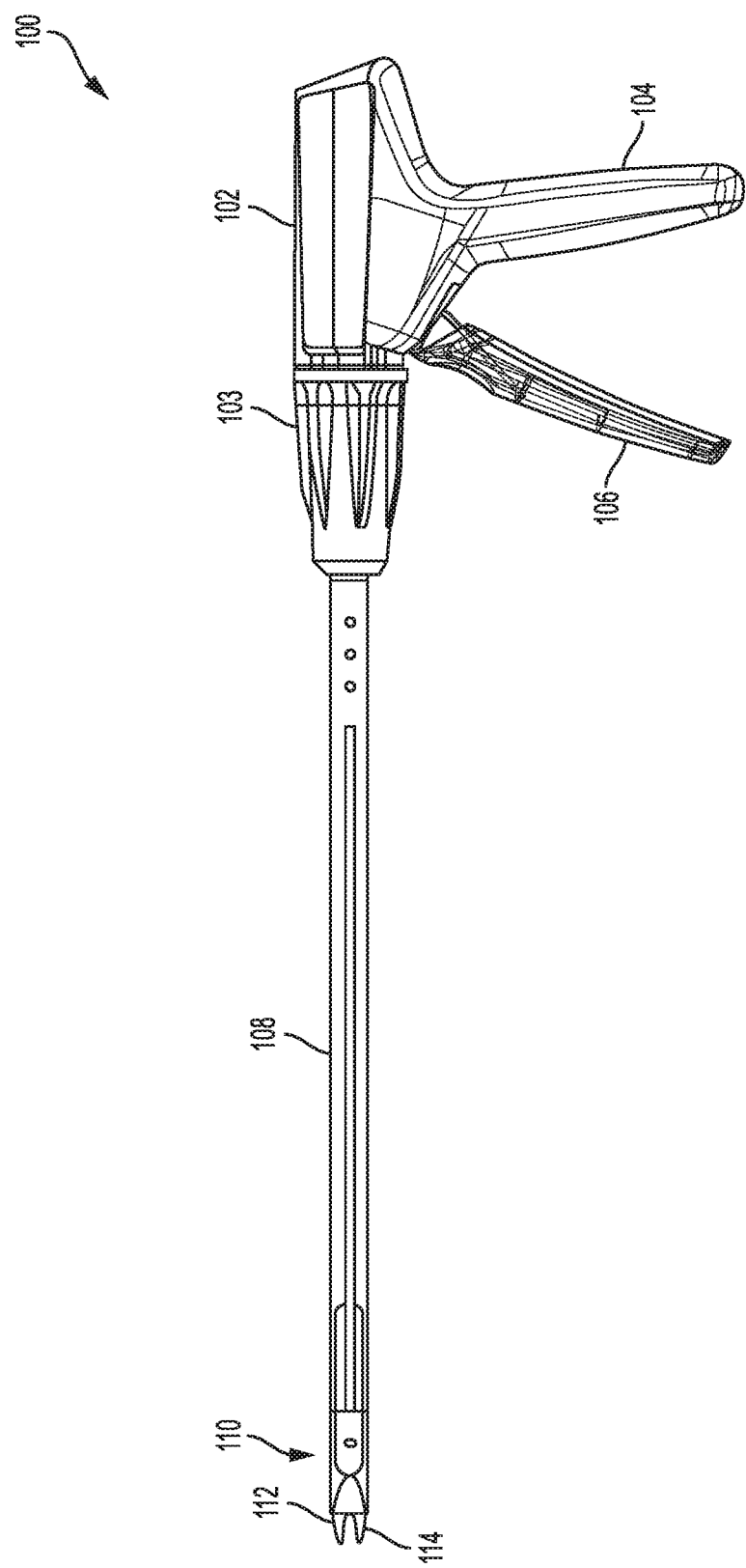
FIG. 1 is a side view of one exemplary embodiment of a surgical clip applier.

Surgical clip appliers and methods are provided for applying surgical clips to tissue, such as a vessel, duct, shunt, etc., during a surgical procedure. The surgical clip applier can include a pair of jaws positioned at a distal end of a shaft extending from a housing, and the pair of jaws can be configured to pivot from an open configuration to a closed configuration to form surgical clips positioned between the jaws. In order for the surgical clips to be properly formed around the tissue, the jaws should at least be properly aligned. However, various forces can be applied to the jaws during use that can force the jaws out of alignment. If the jaws become misaligned, the jaws can scissor during closing, e.g., where one jaws moves past or over the other jaw, resulting in a malformed clip. Furthermore, if the jaws do not sufficiently close to properly form the clip positioned between the jaws, the surgical procedure can either be prolonged or negatively affected. While the jaws should have sufficient strength to withstand the forces applied thereto and to allow for repeated, sequential formation of multiple clips, the jaws should also have some flexibility to accommodate clip formation in thick tissue.

Various embodiments of surgical clip appliers are provided that can include features for assisting with proper functioning of the jaws. For example, some features can assist with maintaining alignment of the jaws, such as maintaining the jaws in a single plane thereby preventing the jaws from scissoring when in the closed configuration. In some embodiments, the jaws can be configured to ensure that opposed inward facing surfaces of the jaws are aligned parallel to each other when the jaws are closed thereby ensuring proper clip formation. Some embodiments can include jaw features and/or be manufactured to allow the jaws to be sufficiently flexible for properly forming clips through thick tissue, while also having sufficient strength for allowing the jaws to maintain their structural integrity thereby allowing the jaws to sequentially form multiple clips. In some embodiments, the surgical clip applier can include a protective cap that can be releasably disposed over the jaws to thereby protect the jaws from damage before use, such as during transport and storing of the surgical clip applier. Furthermore, some embodiments can include features that ensure closure forces are sufficiently transferred along a clip forming mechanism thereby allowing the jaws to close with sufficient force to properly form a clip positioned therebetween. A person skilled in the art will appreciate that the surgical clip applier can include all or only some of these features in any combination and/or can include a variety of other features known in the art. The surgical clip appliers described herein are merely intended to represent certain exemplary embodiments.

FIGS. 1-4B illustrate one embodiment of a surgical clip applier 100. As shown, the surgical clip applier 100 generally includes a housing 102 having a stationary handle 104 and a movable handle or trigger 106 that is pivotally coupled to the housing 102. An elongate shaft 108 extends distally from the housing 102 and includes a jaw assembly 110 formed on a distal end thereof and including first and second jaws 112, 114 that are movable between open and closed positions. The first and second jaws 112, 114 include opposed inward facing surfaces and each inward facing surface has a clip track formed therealong for receiving and guiding legs of a clip into the first and second jaws 112, 114. The elongate shaft 108 can be rotated with respect to the housing 102 via a rotation knob 103.

Figure 2:
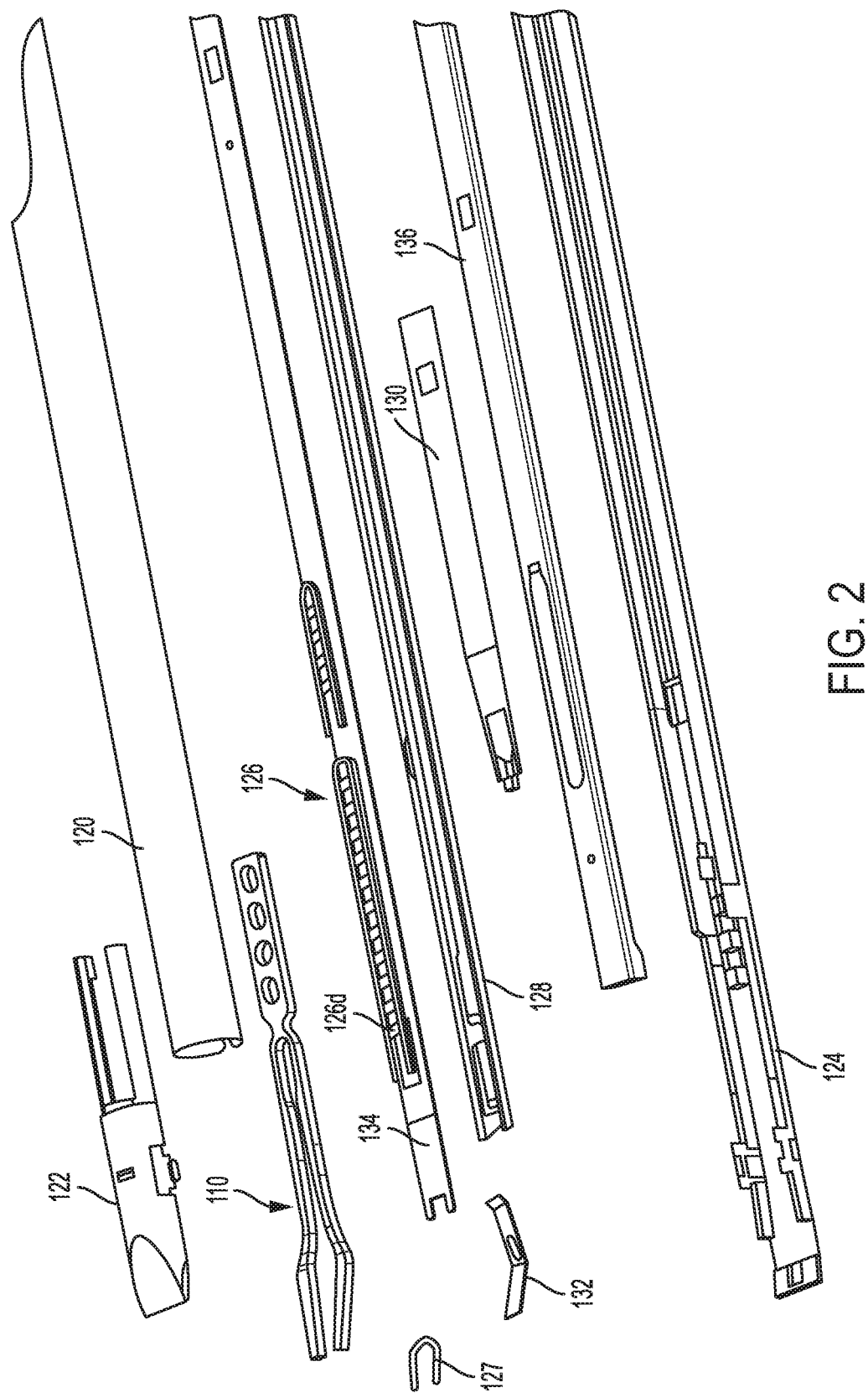
FIG. 2 is an exploded view of a distal portion of the surgical clip applier of FIG. 1.
Figure 3:
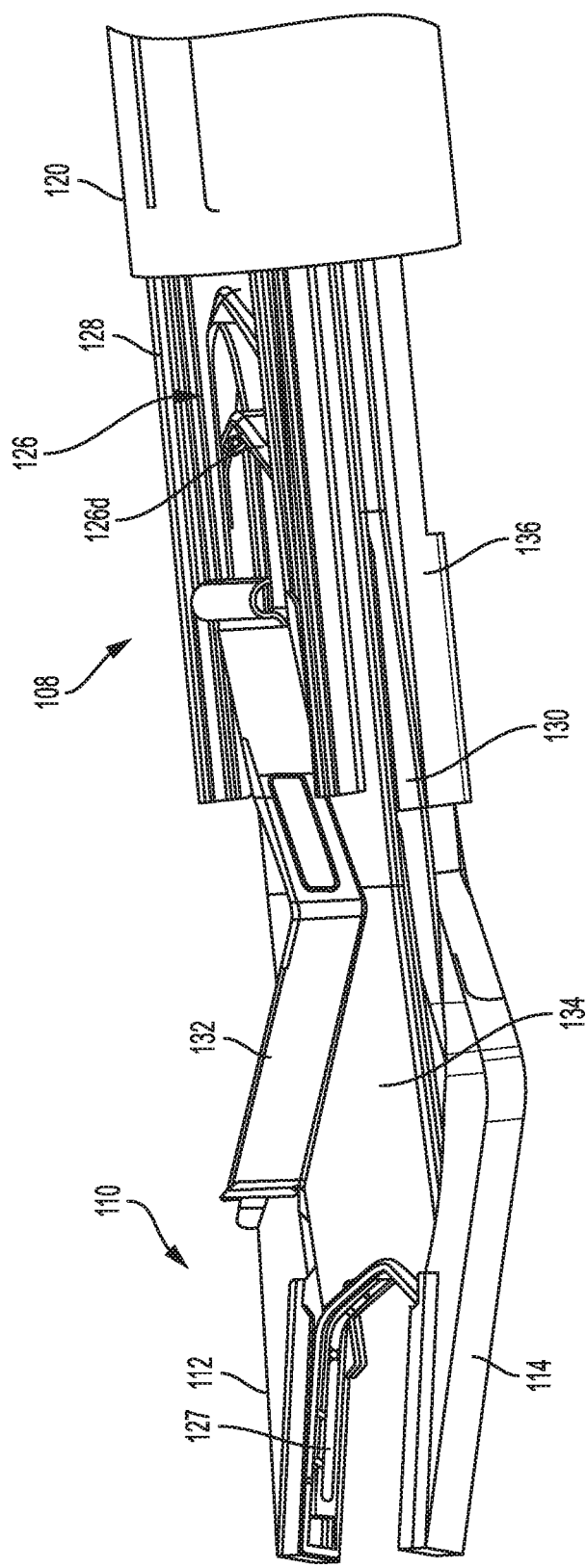
FIG. 3 is a perspective view of a distal portion of the surgical clip applier of FIG. 1.

As shown in FIGS. 2 and 3, the elongate shaft 108 can include an outer support tube 120, an upper shroud 122 coupled distally to the outer support tube 120, and a lower shroud 124. The outer support tube 120 and the upper and lower shrouds 122, 124 form an outer casing of the shaft 108. As shown in FIGS. 2 and 3, a clip stack 126 including multiple surgical clips is disposed within a clip track or holder 128 of the shaft 108 proximal to the first and second jaws 112, 114, and is biased distally. A floor 130 extends beneath the clip stack 126 for maintaining the clip stack 126 in alignment within the shaft 108, and for guiding a distal-most clip 126d into the jaws 112, 114. A lifter spring 132 is positioned just proximal to the jaws 112, 114 and distal to the clip stack 126 for preventing distal movement of the clip stack 126, with the distal-most clip 126d disposed around the lifter spring 132. A feeder bar 134 extends through the elongate shaft 108 for feeding the distal-most clip 126d into the jaws. As shown in FIG. 3 illustrating the clip applier 100 with the upper and lower shrouds 122, 124 removed, a former tube 136 extends around a proximal end of the jaws 112, 114 and is movable distally to cam the jaws 112, 114 to a closed position for forming a clip 127 disposed therebetween.

Figure 4A:
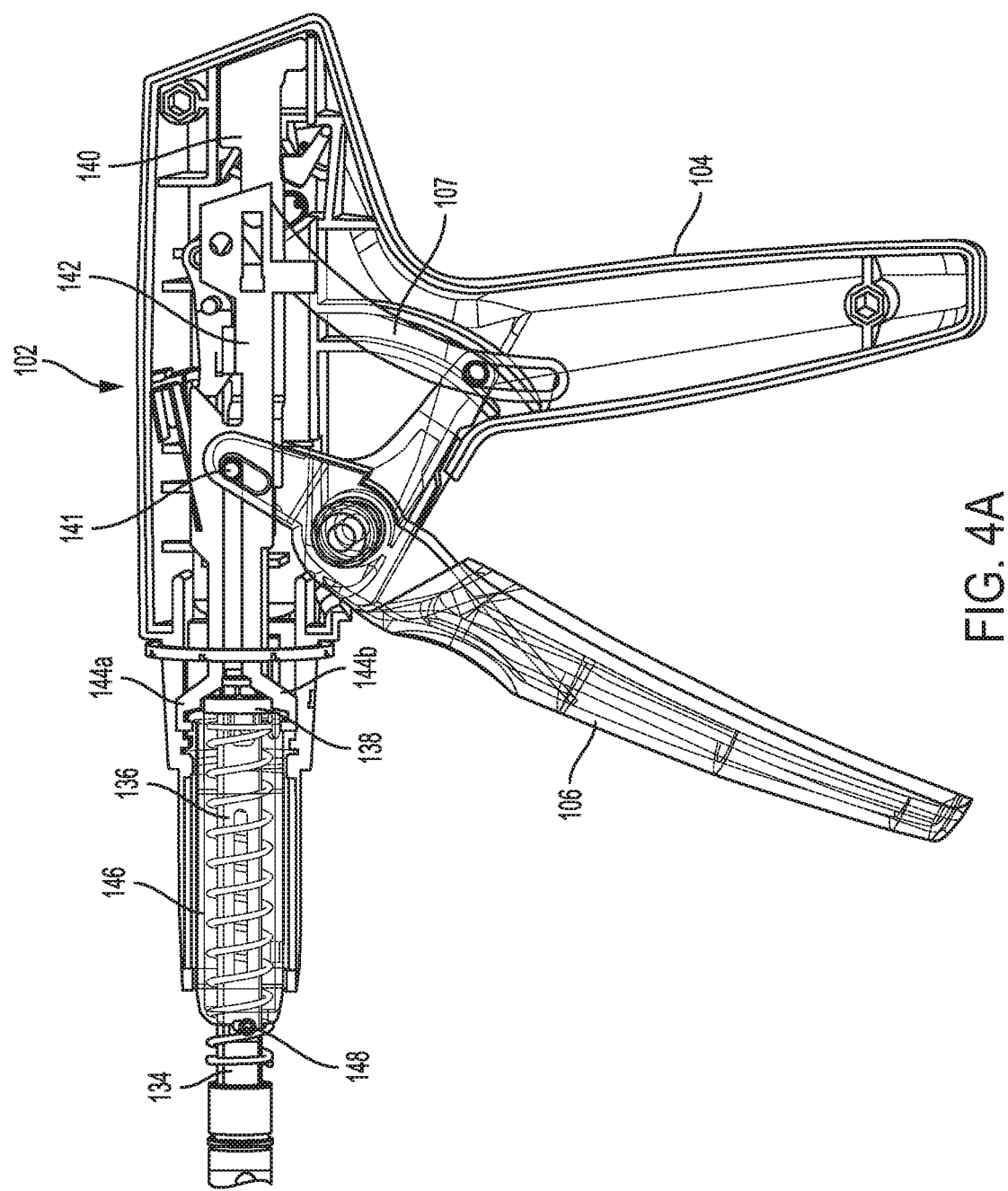
FIG. 4A is a perspective, partially transparent view of a proximal portion of the surgical clip applier of FIG. 1.
Figure 4B:
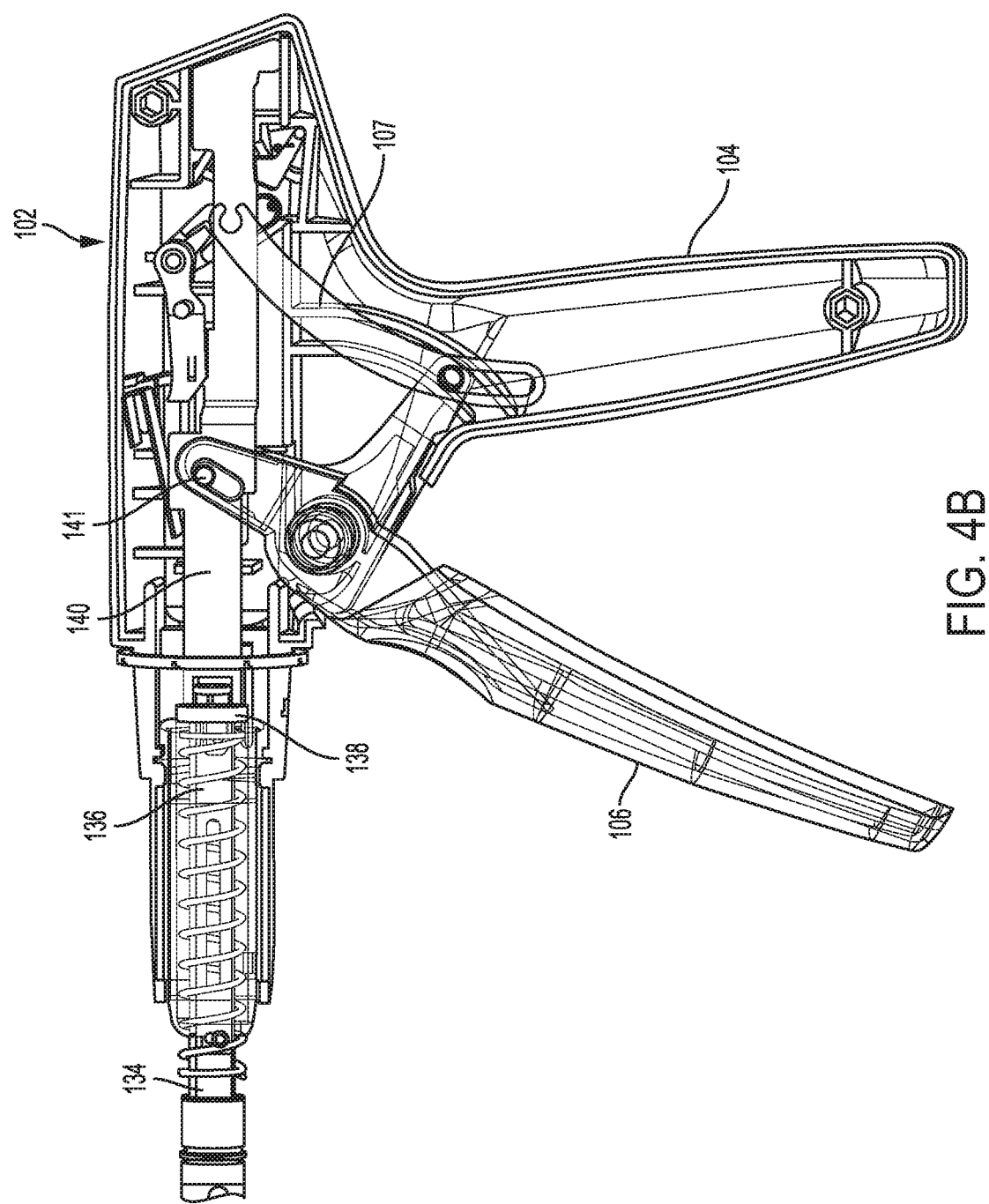
FIG. 4B is another perspective view of the proximal portion of the surgical clip applier of FIG. 1.

The surgical clip applier 100 has a clip forming assembly including various components that operate together to close the jaws 112, 114 when the trigger 106 is activated to thereby cause a clip (e.g., clip 127) disposed in the jaws to be applied (formed) to the tissue. The clip forming assembly encompasses the former tube 136 and other components that are coupled to the trigger 106 configured to be activated to move the former tube 136 distally to thereby close the jaws 112, 114. A clip advancing assembly of the surgical clip applier 100 includes the feeder bar 134 that is also coupled to the trigger 106, via a link 107 extending proximally from the trigger 106, as shown in FIGS. 4A and 4B. In this way, when the trigger 106 is activated, the feeder bar 134 is caused to move proximally, opposite to a distal direction in which the former tube 136 is moved upon activation of the trigger 106.

The clip forming and clip advancing assemblies can have any suitable configurations. For example, in the illustrated embodiment, as shown in FIGS. 4A and 4B, the former tube 136 of the clip forming assembly is coupled, via an inner coupling 138, to a former plate 140 in the housing 102 that is, in turn, coupled to the trigger 106 via a pin 141, and the feeder bar 134 of the clip advancing assembly is coupled to the trigger 106 via a feeder plate 142 that is also coupled to the trigger 106, via the link 107. As shown in FIG. 4A, the feeder plate 142 has arms 144a, 144b at a distal end thereof that are disposed over and mate with a proximal end of an outer coupling 146 (shown partially transparent). A connecting pin 148 at a distal end of the outer coupling 146 attaches the feeder bar 134 to the outer coupling 146. FIGS. 4A and 4B illustrate the housing 102 with part of an outer casing removed, and FIG. 4B shows the housing 102 without the feeder plate 142, for illustration purposes only. It should be appreciated that the surgical clip applier 100 can include various other components and assemblies that are not described herein for the sake of simplicity.

In use, when the trigger 106 of the housing 102 is activated (e.g., moved towards the stationary handle 104), the former plate 140 of the clip forming assembly is advanced distally to cause the former tube 136 to advance distally over the jaws 112, 114, thereby camming the jaws 112, 114 to the closed position. At the same time, the feeder plate 142 of the clip advancing assembly is moved proximally, thereby pulling the feeder bar 134 proximally to position the feeder bar 134 proximal of the distal-most clip 126d of the clip stack 126. Once the clip 127, disposed in the jaws 112, 114 such that clip's legs are received within the clip track of each of the jaws, is fully formed, the trigger 106 is released, which causes the clip forming assembly to move proximally while the clip advancing assembly moves distally. FIG. 2 shows the clip 127 in an original, pre-formed configuration. The proximal movement of the clip forming assembly causes the former tube 136 to retract relative to the jaws, thus allowing the jaws 112, 114 to move to the original open position, thereby releasing the formed clip. The distal movement of the clip advancing assembly causes the feeder bar 134 to move distally, and the feeder bar 134 thereby pushes the distal-most clip 126d distally, overcoming the biasing force of the lifter spring 132 and causing the lifter spring 132 to deflect out of the way, thereby allowing the distal-most clip 126d to be advanced into the jaws 112, 114. In this way, the distal-most clip becomes positioned in the jaws' clip track, like the clip 127 in FIG. 3. The floor 130 helps guide the distal-most clip into the clip tracks of the jaws 112, 114.

Jaw Deformation

As discussed above, it can be beneficial for the jaws of the clip applier to have a balance of flexibility and strength. For example, if the jaws are too stiff, the former tube will be unable to fully compress the jaws towards each other, which can result in inadequately formed clips (e.g., too large of a gap between the formed clip legs). As such, some flexibility of the jaws to allow for full compression of the clip is desired. However, if the jaws are too flexible, the jaws can permanently deform and be unable to properly hold or form a clip.

FIG. 5 illustrates one embodiment of a jaw assembly 210 that includes a proximal part 211 (only a portion is shown) that extends into the shaft 218 and that distally splits into two arms that form the jaws 212, 214. In order to provide sufficient rigidity to allow the jaws 212, 214 to deform a clip 227 therebetween, while allowing some flexibility to ensure a fully formed clip, the jaws 212, 214 can include an intersecting region 219 having an increased width compared to adjacent proximal and distal portions 294, 295 of the jaws 212, 214. This intersecting region 219 with increased width can allow distal-most tips or ends 201 of the jaws 212, 214 to angle toward each other as the jaws 212, 214 close, such as when grasping thick tissue between the jaws 212, 214. By angling the distal-most ends 201 of the jaws 212, 214 toward each other as the jaws 212, 214 close, the distal-most ends 201 can be the first point of contact between the jaws 212, 214. With the distal-most ends 201 in contact, opposed inward facing surfaces 230 of the distal portions 295 of the jaws 212, 214 can be brought together as the former tube 236 is distally advanced along outer contact surfaces 240 of the proximal portions 294 thereby allowing the jaws 212, 214 to fully close and properly form the clip 227 therebetween. By configuring the jaws 212, 214 so the distal-most ends 201 are the first point of contact, this can ensure that the distal-most ends remain in contact as the jaws 212, 214 are further moved to the fully closed configuration, thereby ensuring uniform contact along the opposed inward facing surfaces 230. This can also ensure that a distal end of the clip 227 closes first, thereby capturing targeted tissue and preventing the captured targeted tissue from escaping out of the distal end of the clip 227 during closure of the jaws 212, 214 and formation of the clip 227. In addition, maintaining a positive inward taper of the jaws 212, 214 (e.g., distance between distal ends 201 is less than distance between more proximal inner jaw surfaces) can allow the jaws 212, 214 to retain unformed clips in place for clip formation, including during navigation of the jaws 212, 214 and dissection of the tissue before firing. The intersecting region 219 can also extend along a curve thereby promoting flexibility of the jaws 212, 214 along the curve, while maintaining sufficient strength and rigidity due, at least in part, to the increased width of the intersecting region 219. As such, the intersecting region 219 can allow the jaws 212, 214 to have sufficient flexibility and strength, as desired for sequential clip formation, including when forming clips in thick tissue.

As shown in FIG. 5, when the jaws 212, 214 are open, the proximal part 211 of the jaw assembly 210 can extend approximately parallel to the longitudinal axis L of the shaft 208. Additionally, an angled region 294a of each jaw 212, 214 can extend from the proximal part 211 at a first angle α1 relative to the longitudinal axis L (e.g., the first angle being within a range of approximately 0 degrees to approximately 45 degrees) and in a direction away from the longitudinal axis of the shaft 208. The distal portion 295 of each jaw 212, 214 can include an outer distal surface 296 that extends distally from the angled region 294a and relative to the longitudinal axis L at a second angle α2 (e.g., the second angle being within a range of approximately 0 degrees to approximately 45 degrees) and in a direction towards the longitudinal axis of the shaft 208. Additionally, the distal portions 295 of the jaws 212, 214 can include the opposed inward facing surfaces 230 that extend parallel to the longitudinal axis. Furthermore, the intersecting region 219 can connect the proximal and distal portions 294, 295 of the jaws 212, 214 and it can extend along a curve having a radius within a range of approximately 0.05 inches to approximately 0.50 inches. In addition, the width of the intersecting region 219 can be within a range of approximately 0.05 inches to approximately 0.10 inches, with the width being measured between respective inner and outer surfaces of jaws 212, 214. In an exemplary embodiment, the width at the intersecting region 219 exceeds the width of the remainder of the jaws 212, 214, and thus forms the maximum width of the jaws 212, 214. Although some example dimensions are provided herein, other configurations of an intersecting region 219 positioned between proximal and distal portions of the jaws to assist with providing sufficient flexibility and strength are within the scope of this disclosure.

In some embodiments, in order to achieve a desired strength in each jaw 212, 214, one or both jaws 212, 214 can be heat treated during manufacturing and assembly of the clip applier. Heat treatment temperature and/or duration of heat treatment can be varied to achieve such desired strength in each jaw 212, 214.

Jaw Twist

In another embodiment, the jaws can be formed in the open configuration in a manner that facilitates alignment during closing of the jaws. Many current clip appliers include distal jaws that are angled upward out of a plane extending through the proximal portion of the jaws, as shown in FIG. 5. The opposed inward facing surfaces of the jaws are positioned parallel to each other when the jaws are in the open position. Such a configuration can cause the opposed inward facing surfaces to be non-parallel when the jaws are in the closed position after having traveled along a curved or arched pathway between open and closed positions. If the inner contact surfaces of the jaws are not positioned parallel when the jaws are closed, the jaws can be prevented from properly forming a clip therebetween, and/or can cause formed clip legs to be rotated or scissor relative to each other, thereby detrimentally affecting the ability of the clip to ligate tissue.

Accordingly, FIG. 6 illustrates a cross-sectional view of opposed jaws 312, 314 of another embodiment of a jaw assembly. As shown, the jaws 312, 314 can travel along a curved pathway 313 between open and closed positions. In an exemplary embodiment, the jaws 312, 314 can each include opposed inward facing surfaces 330 that are positioned normal to the pathway 313 such that when the jaws 312, 314 are in the open configuration, the opposed inward facing surfaces 330 are non-parallel to each other. As a result, when the jaws 312, 314 are moved to the closed configuration along the curved pathway 313, the opposed inward facing surfaces 330 will move into a parallel orientation, thereby aligning the inward facing surfaces 330 for proper clip formation.

Upper and Lower Shroud With Interlock

Scissoring or misalignment of the jaws during closing can prevent proper formation of a clip positioned between the jaws and/or can prevent the jaws from sufficiently grasping tissue. Various embodiments of a shroud assembly are thus provided to help prevent misalignment of the jaws during closing.

In general, the shroud assemblies can include at least one mechanical interlock that is configured and/or positioned such that out-of-plane movement of the jaws is prevented. In particular, the mechanical interlock can have a configuration and/or can be at a location that prevents the shroud parts from separating in a direction approximately perpendicular to a plane of motion of the jaws. As a result, the shroud assembly can maintain the jaws in the plane of motion, even when an axial load is applied to the jaws.

Figure 7A:
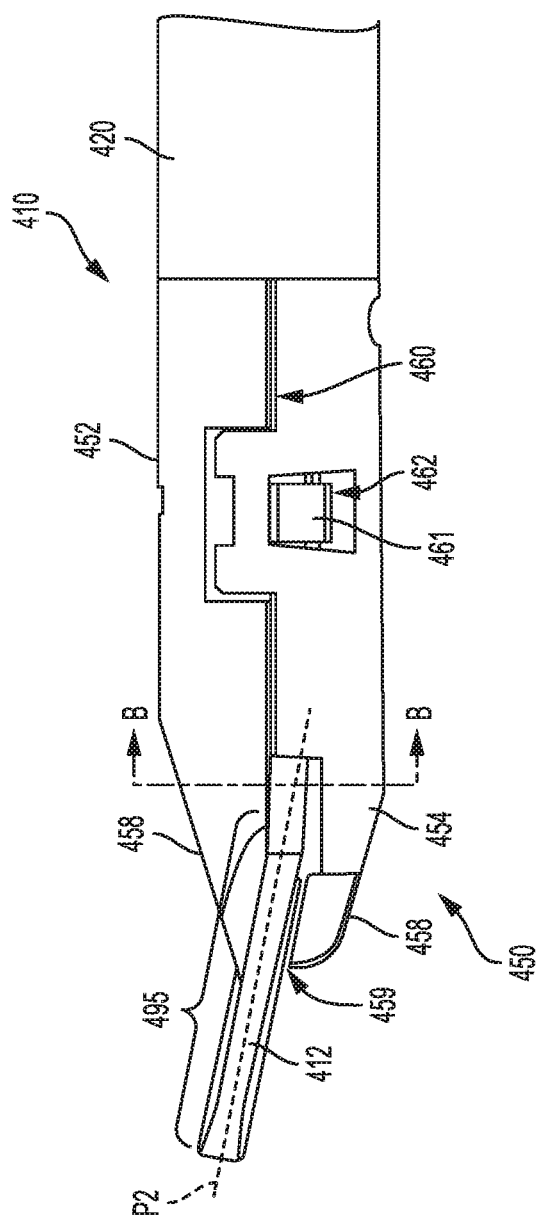
FIG. 7A is a side view of a distal end of another embodiment of a clip applier including a shroud positioned over a part of the jaws.
Figure 7B:
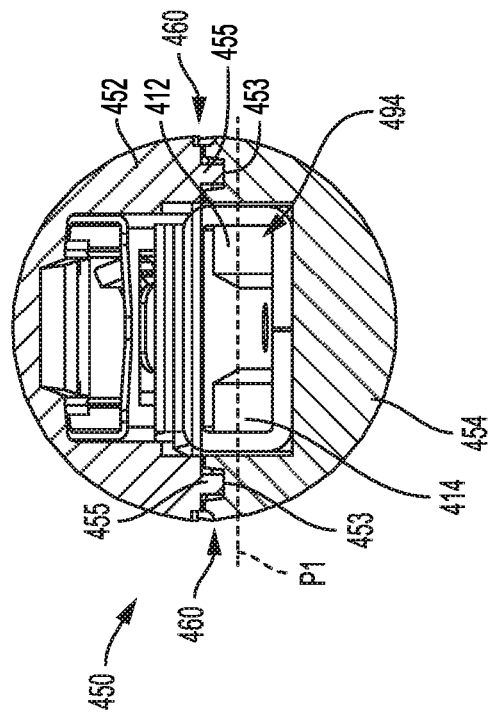
FIG. 7B is a cross-sectional view of the shroud of FIG. 7A showing an embodiment of a mechanical interlock formed between an upper shroud and a lower shroud.

FIGS. 7A and 7B illustrate one embodiment of a shroud assembly 450 that is located at a distal end of an outer support tube 420 of the clip applier 410 and that extends around at least a portion of a pair of jaws 412, 414. As shown, proximal portions 494 of the jaws 412, 414 can extend along a first plane P1 that is coplanar with the longitudinal axis of the outer support tube 420, and distal portions 495 of the jaws 412, 414 can extend along a second plane P2 positioned at an angle relative to the first plane.

The shroud assembly 450 can include an upper shroud 452 and a lower shroud 454. Each shroud 452, 454 can have a generally hemi-cylindrical shape with a tapered distal end 458. When the upper and lower shrouds 452, 454 are coupled together, as shown in FIG. 7A, the shroud assembly 450 can be cylindrical with the tapered distal ends 458 of the upper and lower shrouds 452, 454 angled toward each other. A space 459 can be formed between the coupled upper and lower shrouds 452, 454, and the space 459 can be sized and configured to allow the jaws 412, 414 to extend therethrough.

As shown in FIG. 7A, the space 459 can extend at an angle between the tapered distal ends 458 of the upper and lower shrouds 452, 454 to accommodate the angled distal portions 495 of the jaws 412, 414. In particular, at least a distal portion of the space 459 can extend along the second plane to thereby align with the distal portions 495 of the jaws 412, 414. The height of the space 459 or distance between the tapered distal ends 458 can allow the jaws 412, 414 to move along the second plane between open and closed configurations, while preventing the jaws 412, 414 from moving out of the second plane and becoming misaligned, such as when in the closed configuration. For example, in some embodiments, the upper and lower shrouds 452, 454 can engage and maintain at least a portion of the proximal portion 494 of the jaws 412, 414 in the first plane, and/or the upper and lower shrouds 452, 454 can engage and maintain at least a portion of the distal portion 495 of the jaws 412, 414 in the second plane. Such maintaining of the proximal and/or distal portions 494, 495 along the first and/or second planes, respectively, by the shroud assembly can prevent the jaws 412, 414 from becoming misaligned, even when an axial load is applied to the jaws 412, 414.

The space 459 and/or tapered distal ends 458 of the upper and lower shrouds 452, 454 can have a variety of shapes that prevent misalignment of the jaws 412, 414 while allowing the jaws 412, 414 to follow a pathway extending between open and closed configurations of the jaws. For example, the pathway can be either linear or curved and the upper and lower shrouds 452, 454 can have similar linear and/or curved features to thereby allow the jaws 412, 414 to follow along the pathway without becoming misaligned. In general, the space 459 includes a height that is slightly larger than a distance between top and bottom surfaces of the jaws 412, 414. For example, the top and bottom surfaces of the jaws 412, 414 can slidably mate with opposing bottom and top surfaces of the upper and lower shrouds 452, 454, respectively, that form the space 459.

To assist the shroud assembly 450 with preventing misalignment of the jaws 412, 414, the shroud assembly 450 can include at least one mechanical interlock 460 between the upper and lower shrouds 452, 454 that prevents movement between the upper and lower shrouds 452, 454 and results in a stiffer and more structurally robust shroud assembly 450. The mechanical interlocks 460 can thus assist with maintaining the shape and configuration of the space 459 between the upper and lower shrouds 452, 454 which, as discussed above, assists with constraining the movement of the jaws 412, 414 to along defined planes and/or pathways thereby preventing misalignment of the jaws 412, 414.

For example, the shroud assembly illustrated in FIGS. 7A and 7B includes an embodiment of the mechanical interlock 460 having engaging features that are welded together, such as ultrasonically welded, thereby forming a mechanical interlock. More specifically, the lower shroud 454 can include a recess 453 that extends longitudinally along opposing sides of a top side of the lower shroud 454. Additionally, the upper shroud 452 can include a ridge 455 that extends longitudinally along opposing sides of a bottom side of the upper shroud 452. As shown in FIG. 7B, the recess 453 can be shaped to receive the ridge 455. However, one or more recesses 453 and/or ridges 455 can extend along either the upper or lower shroud 452, 454. As such, during assembly of the shroud assembly 450, the upper and lower shrouds 452, 454 can be coupled together such that each ridge 455 is seated within a corresponding recess 453. Once seated, the ridge 455 and recess 453 coupling can limit movement between the upper and lower shrouds 452, 454. Furthermore, the ridge 455 and recess 453 can be welded together thereby permanently securing the upper and lower shrouds 452, 454 together. Such welding of the upper and lower shrouds 452, 454 can prevent movement between the upper and lower shrouds 452, 454 thereby increasing the stiffness of the shroud assembly 450 and ensuring that the upper and lower shrouds 452, 454 do not separate during use, including when a load is applied to either of the jaws 412, 414 or shroud assembly 450. In some embodiments, an adhesive can be used as alternative to using ultrasonic welding for permanently securing the upper and lower shrouds 452, 454 together.

Other mechanical interlocks formed between the upper and lower shrouds 452, 454 have been contemplated for ensuring that the jaws 412, 414 do not become misaligned, of which some are described in more detail below. FIG. 7A illustrates an additional mechanical interlock formed between the shrouds, however this interlock allows some clearance therebetween for limiting, but not entirely preventing, movement between the upper and lower shrouds 452, 454. For example, the upper shroud 452 can include spring tabs 461 extending from opposing sides of the upper shroud 452, and the lower shroud 454 can include angled thru-holes 462 that extend through opposing sides of the lower shroud 454. The spring tabs 461 can be configured to extend into and securely couple to a part of the angled thru-holes 462 thereby forming a mechanical interlock that couples and limits movement between the upper and lower shrouds 452, 454.

FIGS. 8A and 8B illustrate another embodiment of a shroud assembly 550 that is similar to the shroud assembly described above and illustrated in FIGS. 7A and 7B, including upper and lower shrouds 552, 554 that, when coupled together, form a space 559 therebetween that that prevents the jaws from becoming misaligned at least when the jaws are in the closed position. The shroud assembly 550 illustrated in FIGS. 8A and 8B includes another embodiment of a mechanical interlock 560 formed between the upper and lower shrouds 552, 554. The mechanical interlock 560 can assist with securing the coupling of the upper and lower shrouds 552, 554 and preventing movement therebetween thereby preventing misalignment of the jaws. As with the previous embodiment, while not discussed, the shroud can include additional mechanical interlocks.

As shown in FIG. 8B, the upper shroud 552 can include a pair of first keyed tracks 553 formed along opposing inner side walls of the upper shroud 552, and the lower shroud 554 can include a pair of second keyed tracks 555 formed along opposing side walls of the lower shroud 554. The first keyed track 553 can slidably mate with the second keyed track 555. The tolerance between the first and second keyed tracks 553, 555 can be configured such that little to no axial movement between the upper and lower shrouds 552, 554 is allowed to occur. The mechanical interlock between the shrouds 552, 554 can also be configured to prevent separation between the upper and lower shrouds 552, 554, i.e., movement radially outward from one another, including when a load is applied to the shroud assembly 550 or jaws, thereby preventing misalignment of the jaws. In some embodiments, the first and second keyed tracks 553, 555 can further be welded together.

FIGS. 9A-9E illustrate another embodiment of a shroud assembly 650 that is similar to the shroud assembly described above and illustrated in FIGS. 7A and 7B, including upper and lower shrouds 652, 654 that, when coupled together, form a space 659 therebetween that prevents the jaws from becoming misaligned at least when the jaws are in the closed configuration. The shroud assembly 650 illustrated in FIGS. 9A-9E includes another embodiment of a mechanical interlock 660 formed between the upper and lower shrouds 652, 654 that prevents movement between the shrouds to assist in preventing misalignment of the jaws.

As show in FIG. 9A, the upper shroud 652 includes at least one pair of engaging features 670 extending approximately perpendicular from opposing inner sides of the upper shroud 652. The engaging features 670 can each be in the form of an L-shaped extension or protrusion that extends approximately perpendicular from the respective inner side of the upper shroud 652. As shown in FIG. 9B, the lower shroud 654 can include rails 677 extending along opposed sides thereof and defining a locking track 675. In particular, each rail 677 can be generally L-shaped and oriented in a direction opposite to the engaging features 670. The rails 677 can include at least one pair of cut-outs or slots 672 formed therein along opposing sides of the lower shroud 654.

Figure 9C:
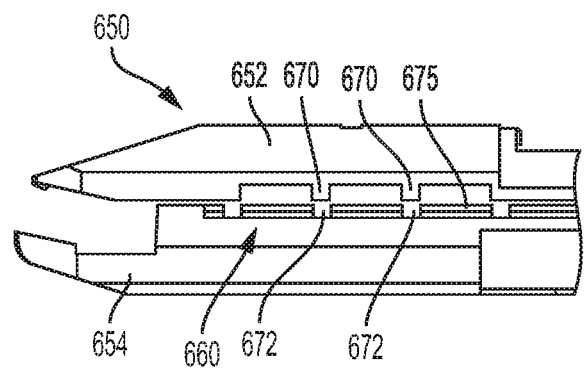
FIG. 9C is a side view of yet another embodiment of a mechanical interlock formed between the upper and lower shrouds of FIGS. 9A and 9B forming the shroud assembly.
Figure 9D:
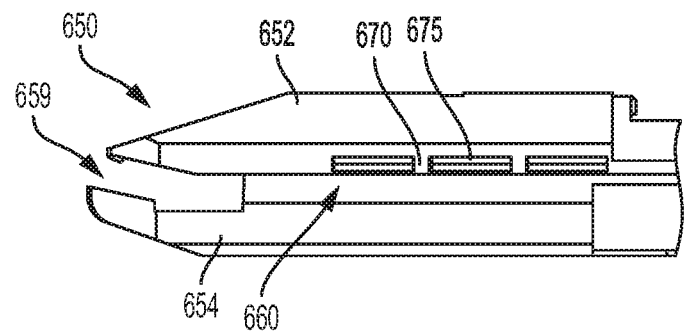
FIG. 9D is a side view of the shroud assembly of FIG. 9C showing the upper shroud engaged with and distally translating relative to the lower shroud.
Figure 9E:
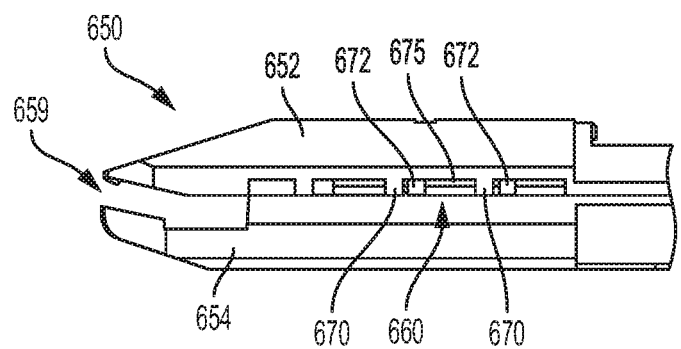
FIG. 9E is a side view of the shroud assembly of FIG. 9C showing the upper shroud in a secured distal position configured to prevent misalignment of jaws extending therethrough.

The engaging features 670 can be configured to extend through the slots 672 and to slide under the rails 677 to form a mechanical interlock. As shown in FIG. 9C, the locking tracks 675 can be oriented along the lower shroud 654 such that the locking tracks 675 can accept corresponding engaging features 670 traveling along an approximately linear path that is perpendicular to the longitudinal axis of the shroud assembly 650. As shown in FIG. 9D, once the engaging features 670 have passed through the slots 672 and have reached the locking track 675, the upper shroud 652 can be translated (e.g., distally or proximally) thereby translating the engaging features 670 along the locking track 675 until the upper shroud 652 is properly positioned relative to the lower shroud 654 (e.g., distal ends of the upper and lower shrouds 652, 654 are vertically aligned). In some embodiments, a mechanical stop (e.g., a ledge or wall at a distal end of the locking track 675) can prevent the upper shroud 652 from translating beyond a desired position, such as the position of the upper shroud relative to lower shroud shown in FIG. 9E where the space 659 is properly formed for preventing misalignment of the jaws. However, other mechanical stops can be included to assist with correctly positioning the upper shroud 652 relative to the lower shroud 654 to thereby allow the shroud assembly 650 to prevent misalignment of the jaws. Furthermore, the tolerance between the engaging features 670 and the locking track 675 can be sufficiently small such that that little to no axial movement between the upper and lower shrouds 652, 654 is allowed to occur. This can also result in a mechanical interlock with sufficient stiffness of the shroud assembly 650 to thereby prevent separation between the upper and lower shrouds 652, 654, including when a load is applied to the shroud assembly 650 or jaws, as well as prevent misalignment of the jaws.

Figure 10A:
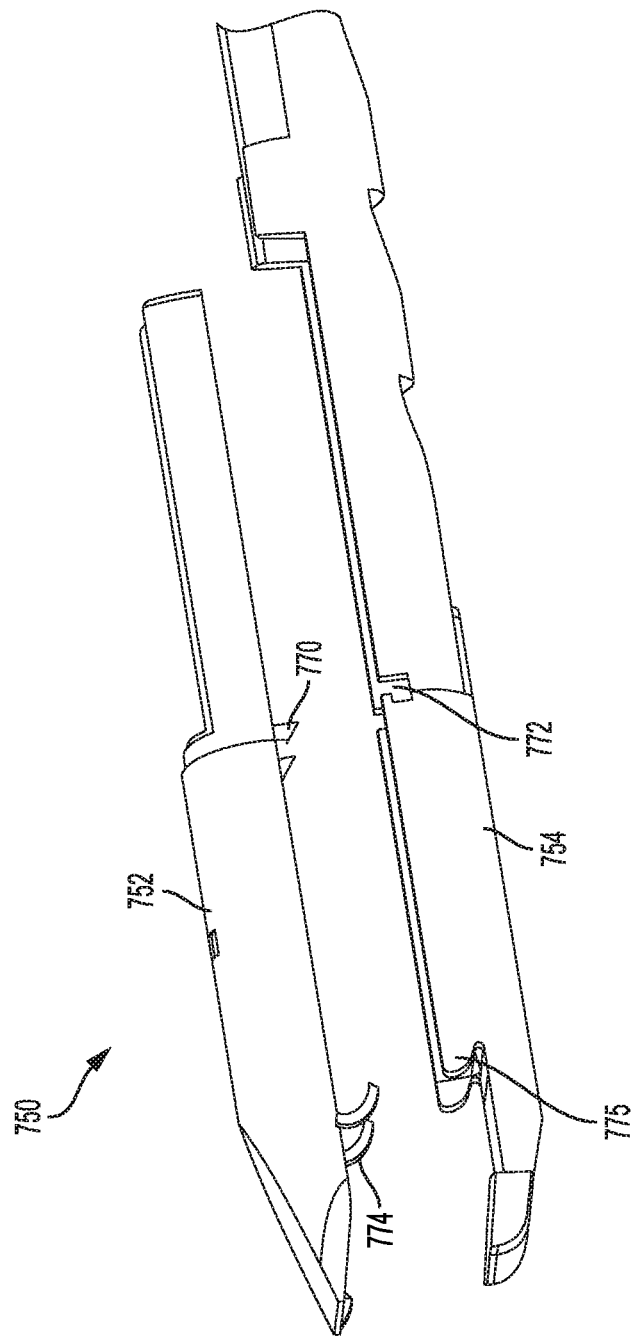
FIG. 10A is an exploded perspective side view of yet another embodiment of upper and lower shrouds that are configured to be coupled together to form a shroud assembly having at least one mechanical interlock.
Figure 10B:
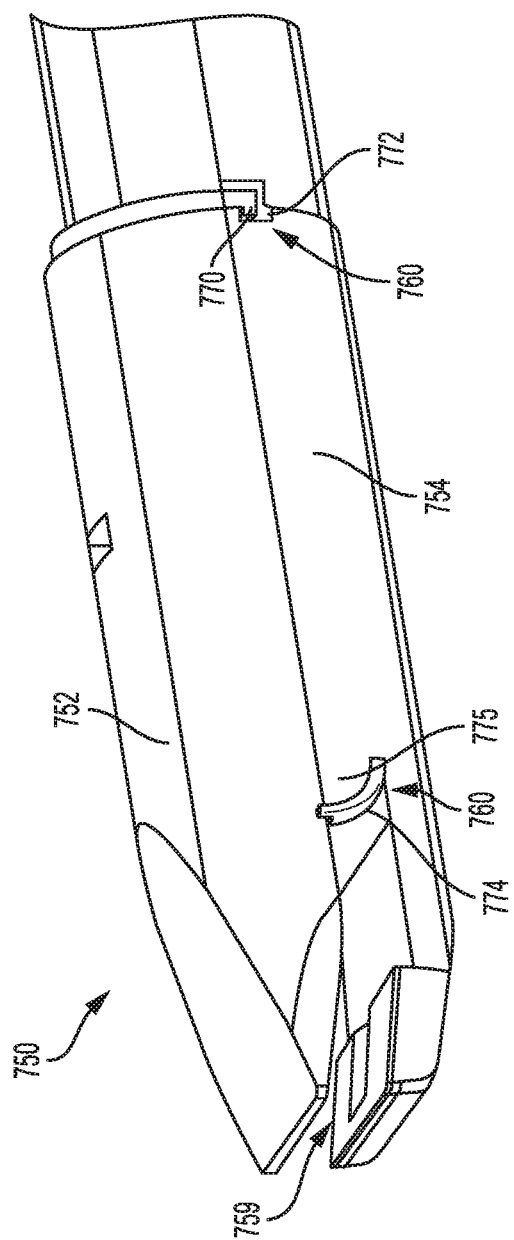
FIG. 10B is a side perspective view of the upper and lower shrouds of FIG. 14A coupled together to form the shroud assembly.

FIGS. 10A and 10B illustrate yet another embodiment of a shroud assembly 750 that is similar to the shroud assembly described above and illustrated in FIGS. 7A and 7B, including having upper and lower shrouds 752, 754 that, when coupled together, form a space 759 therebetween that assists with preventing the jaws from becoming misaligned at least when the jaws are in the closed position. The shroud assembly 750 illustrated in FIGS. 10A and 10B includes another embodiment of a mechanical interlock 760 formed between the upper and lower shrouds 752, 754. In this embodiment, the upper shroud 752 is pivotally matable to the lower shroud 754 for coupling the upper shroud 752 to the lower shroud 754. For example, the upper shroud 752 can include a pair of hook features 774 positioned adjacent a distal end and extending from opposing sides of a bottom side of the upper shroud 752. The lower shroud 754 can include a pair of curved slots 775 positioned adjacent a distal end and along opposing sides of the lower shroud 754. Furthermore, the upper shroud 752 can include a pair of spring flanges 770 that extend from a bottom side of opposing sides of the upper shroud 752. The lower shroud 754 can include a pair of associated hooked grooves 772 along opposing sides of the lower shroud 754. Although the above features are described relative to the upper or lower shrouds 752, 754, the upper and/or lower shrouds 752, 754 can include any features described herein. For example, the lower shroud 754 can include the pair of hook features 774 and the upper shroud 752 can include the pair of curved slots 775.

The hook features 774 can be configured to slidably engage the curved slots 775 and, when slidably engaged, allow the proximal end of the upper shroud 752 to pivot towards the lower shroud 754 thereby allowing the spring flanges 770 to securely engage the hooked grooves 772. Each spring flange 770 can flex to allow insertion into the respective hooked groove 772 until a flanged end of the spring flange 770 is allowed to engage a recess in the hooked groove 772 thereby returning the spring flange 770 to its original non-flexed position and securely mating the upper shroud to the lower shroud, as shown in FIG. 10B.

The mechanical interlocks 760 that form the secure couplings between the upper and lower shroud 752, 754 can cause sufficient stiffness between the upper and lower shrouds 752, 754 such that the space 759 formed between the upper and lower shrouds 752, 754 can not deform, such as when a load is applied to either the jaws or the shroud assembly 750. As such the mechanical interlock 760 can assist with preventing misalignment of the jaws.

FIG. 11 illustrates another embodiment of a shroud assembly 850 that is similar to the shroud assembly described above and illustrated in FIGS. 7A and 7B, including having upper and lower shrouds 852, 854 that form a space 859 therebetween that assists with preventing the jaws from becoming misaligned at least when the jaws are in the closed position. The shroud assembly 850 illustrated in FIG. 11 includes yet another embodiment of a mechanical interlock 860 formed between mating ends 851 of first and second sides 850a, 850b of the shroud assembly 850. In this embodiment, the shroud assembly 850 includes first and second sides 850a, 850b that mate together, rather than top and bottom shrouds. As such, the mating ends 851 can run along top and bottom sides of the shroud assembly 850 when the first and second sides 850a, 850b are coupled together. Additionally, the mating ends 851 can be configured to securely couple together (e.g., snap fit together and/or using any of the coupling features described herein for coupling upper and lower shrouds 852, 854 together) thereby allowing little to no axial movement between the first and second sides 850a, 850b of the shroud assembly 850. By positioning the mechanical interlock 860 along the top and bottom of the shroud assembly 850, axial loads applied to at least the jaws can be perpendicular to the mechanical interlock 860 thereby resulting in sufficient stiffness of the shroud assembly 850 to prevent deformation of the space 859 and misalignment of the jaws.

Figure 12:
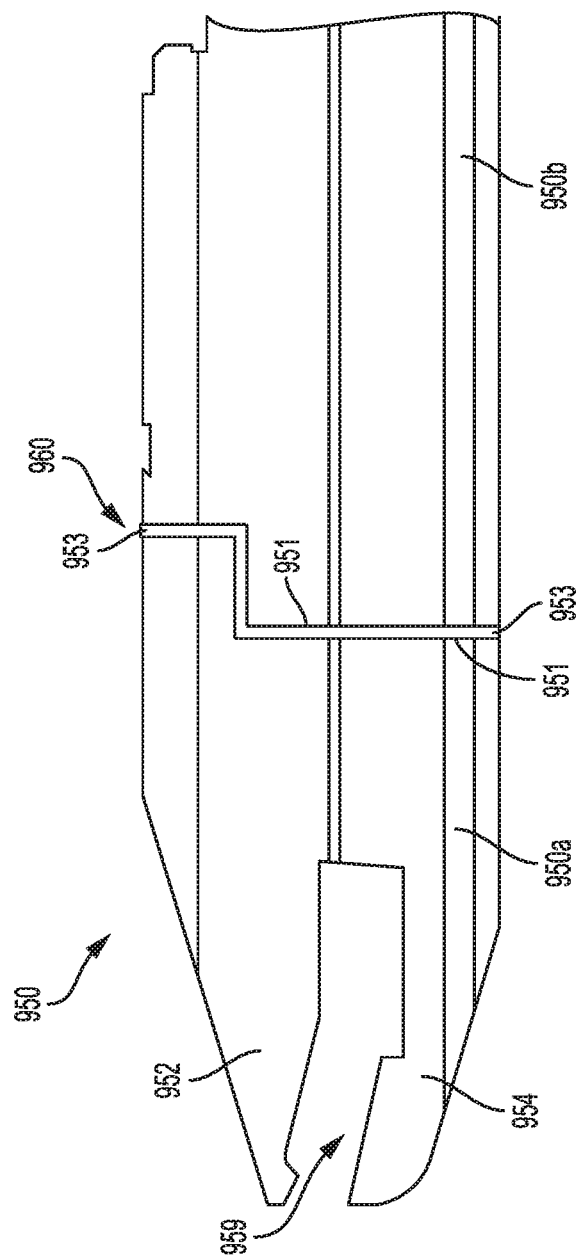
FIG. 12 is a side view of yet another embodiment of a mechanical interlock formed between distal and proximal parts of a shroud assembly.

FIG. 12 illustrates another embodiment of a shroud assembly 950 that is similar to the shroud assembly described above and illustrated in FIGS. 7A-7B, including having upper and lower shrouds 952, 954 that form a space 959 therebetween that assists with preventing the jaws from becoming misaligned at least when the jaws are in the closed position. The shroud assembly 950 illustrated in FIG. 12 also includes another embodiment of a mechanical interlock 960. In this embodiment, the shroud assembly 950 includes distal and proximal parts 950a, 950b that mate together. As such, the mechanical interlock 960 is formed between mating ends 951 of distal and proximal parts 950a, 950b of the shroud assembly 950. When the distal and proximal parts 950a, 950b are coupled together, the mating ends extend around a circumference of the shroud assembly, as shown in FIG. 12. Furthermore, the mating ends 951 of the distal and proximal parts 950a, 950b can be asymmetric such that they couple together and position coupling features (e.g., snap-fit couplings 953) along a top and bottom side of the shroud assembly 950 that are offset from each other, as shown in FIG. 12.

The asymmetrical mating ends 951 and positioning of the snap-fit couplings 953 along the top and bottom sides of the shroud assembly 950 can allow axial loads to be directed away from the snap-fit couplings 953 thereby preventing disruption of the coupling between the snap-fit couplings 953 and allowing the shroud assembly 950 to maintain its structural integrity. This can further allow the shroud assembly 950 to prevent the jaws from becoming misaligned, such as by preserving the size and configuration of the space 959 formed between the upper and lower shrouds 952, 954.

FIG. 13 illustrates a cross-sectional view of another embodiment of a shroud assembly 1050 having a mechanical interlock 1060 formed between upper and lower shrouds 1052, 1054. The embodiment of the mechanical interlock 1060 of shroud assembly 1050 shown in FIG. 13 includes a reinforcement structure 1090 (e.g., steel pin) that extends along a reinforcement pathway 1091 extending through a coupling between the upper and lower shrouds 1052, 1054. The coupling can include, for example, interlocking extensions or tabs 1093 extending from the upper and lower shrouds 1052, 1054. The tabs 1093 can each include a passageway that forms the reinforcement pathway 1091 when the tabs 1093 are interlocked. The reinforcement structure 1090 can be advanced along the reinforcement pathway 1091, which can provide a tight-tolerance sliding fit to thereby limit or prevent movement between the upper and lower shrouds 1052, 1054. As such, the shroud assembly 1050 can be sufficiently stiff to thereby prevent separation between the upper and lower shrouds 1052, 1054, including when a load is applied to the shroud assembly 1050 or jaws, as well as prevent misalignment of the jaws.

Any of the shroud assemblies described herein can be made out of a variety of materials, including rigid materials, such as steel, aluminum, and plastic to prevent deformation of the shroud assembly and/or the space to allow the shroud assembly to effectively prevent the jaws from becoming misaligned. Placement of the shroud assembly relative to the jaws can also vary. For example, the shroud assembly can extend a variety of lengths over the proximal portion and/or distal portion of the jaws members. As such, the shroud assembly can engage a variety of positions along the jaws to thereby maintain alignment of the jaws.

Hook Feature on Former Plate

In other embodiments, features can be provided to assist in transferring forces from the proximal handle of a clip applier device to the end effector. As previously described herein with respect to FIGS. 4A-4B, the clip applier can including a clip forming assembly that is advanced distally when the trigger is actuated to advance a former tube over the jaws to close the jaws and therefore form a clip disposed between the jaws. As was also previously explained herein, the clip applier can also include a clip feeding assembly that is retracted when the clip forming assembly is advanced, and that is advanced distally to feed a clip into the jaws when the clip forming assembly is retracted. As a result of these two assemblies being driven through the same shaft, the clip forming assembly can include components in the housing that are offset from the longitudinal axis of the shaft. This offset configuration can cause components to become misaligned or can otherwise cause a loss in force between the proximal and distal ends of the device. Accordingly, in order to prevent a loss of force, an alignment and engagement mechanism is provided herein for maintaining a coupling between components of the clip forming assembly, thereby ensuring efficient and effective transfer of jaw closure forces along the clip forming assembly.

FIGS. 14A-14C illustrate a portion of the clip applier 100 of FIGS. 1-4B in more detail, showing a clip forming assembly that includes a former plate 140 extending through the housing 102 of the clip applier 100. The former plate 140 can be coupled, via an inner coupling 138, to the former tube 136 (shown, for example, in FIGS. 4A and 4B) that can be advanced distally by the former plate 140 to cam the jaws to a closed position for forming a clip therebetween. For example, the trigger 106 can be actuated (e.g., pivoted) to cause the former plate 140 to distally advance thereby distally advancing the inner coupling 138, which causes the jaws to form the closed configuration.

As shown in FIG. 14B, the former plate 140 can extend along a plane that is offset from a longitudinal axis of the inner coupling 138. Furthermore, manufacturing and assembly tolerances incorporated in the connection between the inner coupling 138 and the former tube 136 can cause the inner coupling 138 to slightly pivot in the direction that the former plate 140 is offset from the longitudinal axis of the inner coupling 138 as the former plate 140 applies a force against the inner coupling 138. As a result, when the former plate 140 is distally advanced against the inner coupling 138, the former plate 140 can tend to slide along the pivoted inner coupling 138 and deflect laterally in the direction to which it is offset from the longitudinal axis of the inner coupling 138.

In order to prevent such lateral deflection of the former plate 140, the former plate can include a hook feature 1217 at a distal end that is configured to extend around a side of a proximal end of the inner coupling 138, such as around an extension 1245 extending proximally from the proximal end of the inner coupling 138. As shown in more detail in FIG. 15C, the hook feature 1217 can be a circular or u-shaped and can extend transverse to a longitudinal axis of the former plate. The hook feature 1217 can include a circular inner diameter that slidably mates with a groove formed in the extension 1245 of the inner coupling 138. As such, the hook feature 1217 can allow the inner coupling 138 to rotate relative to the former plate 140, such as during shaft rotation, while still engaging the inner coupling 138 for axially moving the inner coupling 138 (and former tube 136). In particular, as shown in FIG. 14B, the hook feature 1217 can be concentric with at least the extension 1245 and positioned on one side of and in engagement with the extension 1245 such that distal movement of the former plate 140 can cause efficient and effective distal movement of the inner coupling 138 while allowing rotation of the shaft and the inner coupling 138 relative to the housing 102 and the former plate 140. The hook feature 1217 can include a proximal surface 1219 that can mate against a distal surface of the extension 1245 such that proximal translation of the former plate 140 can allow the proximal surface 1219 of the hook feature 1217 to apply a force on the distal surface of the extension 1245 thereby pulling the inner coupling 138 and former tube 136 in the proximal direction and opening the jaws. This can allow the user to manipulate the trigger 106 (e.g., force the trigger 106 into the unactuated position) to thereby force the jaws open, such as if the jaws have become stuck in a closed or partially closed position.

The hook feature 1217 of the former plate 140 can be configured to extend around a side of the extension 1245 that is opposite from the direction of offset of the former plate 140 relative to the longitudinal axis of the inner coupling 138. This configuration can prevent the former plate 140 from deflecting laterally away the longitudinal axis of the inner coupling 138 as the former plate 140 applies a force against the inner coupling 138 to thereby cause the former tube 136 to translate in the distal direction. The hook feature 1217 can thus assist the former plate 140 with transmitting as much load as possible to the inner coupling 138 thereby efficiently and effectively distally translating the inner coupling 138 and former tube and moving the jaws into the closed configuration. Furthermore, in some embodiments, another part of the clip applier (e.g., the feeder plate 142, as shown in FIG. 4A) can be positioned along a side of the former plate 140 that is directed towards the longitudinal axis of the inner coupling 138 thereby preventing the former plate from deflecting laterally towards the longitudinal axis of the inner coupling 138.

Other embodiments of the hook feature 1217 having different shapes and configurations are within the scope of this disclosure, such as shown in FIGS. 14D and 14E. For example, FIG. 14D illustrates another embodiment of the hook feature 2217 that can include a space 2219 formed during manufacturing (e.g., during stamp-forming of the hook feature 2217). This can reduce or eliminate stretching of the material to form the hook feature 2217 during manufacturing thereby resulting in a more rigid and structurally strong hook feature 2217 compared to stretching the material during manufacturing to form the hook feature. As shown in FIG. 14D, the space can be positioned along the hook portion of the hook feature 2217 thereby forming a pair of partial hook features separated by the space 2219. However, as shown in FIG. 14E, a space 3219 can be formed at an end of the hook feature 3217.

Protective Cap

In order to protect the jaws and prevent deformation or damage to the jaws, e.g., during shipping, a protective cap is provided that can be releasably disposed over an end effector of a clip applier. The cap can be formed from a hard rigid plastic to protect the jaws from damage prior to use, including during removal of the cap, thereby reducing surgical errors due to malfunctioning jaws. The cap can be removed by a user to allow the clip applier to be used in a procedure.

Figure 15B:
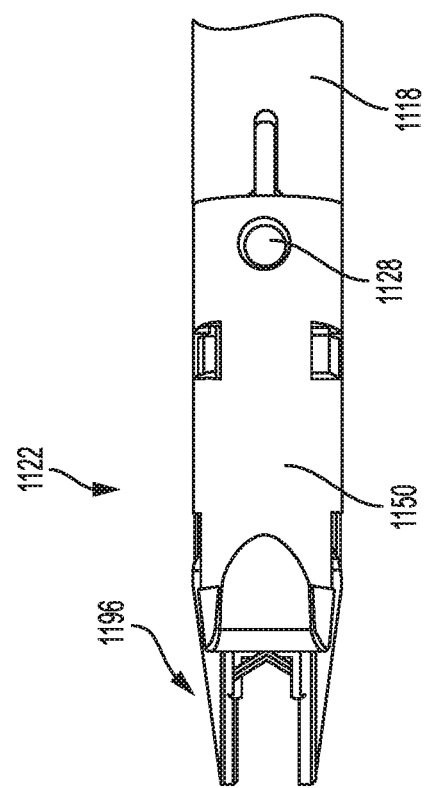
FIG. 15B is a bottom view of the end effector of FIG. 15A.
Figure 15A:
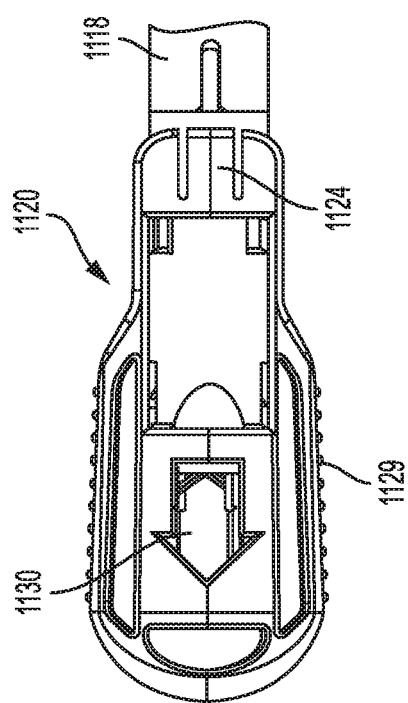
FIG. 15A is a top view of an embodiment of a protective cap that is configured to be removably secured to an end effector of the clip applier.
Figure 15C:
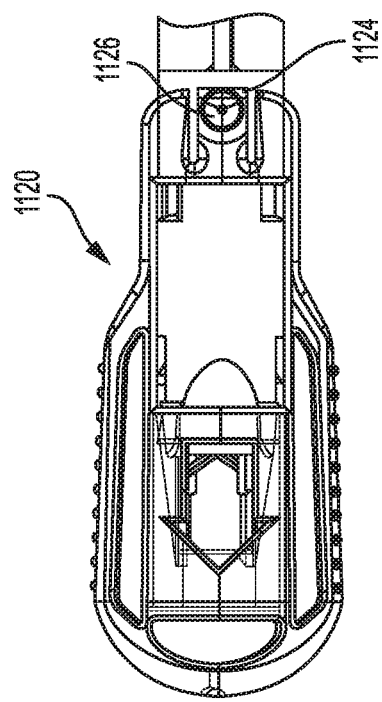
FIG. 15C is a top partially transparent view of the protective cap and end effector of FIG. 15A.

FIGS. 15A-15C illustrate one embodiment of a cap 1120 that is configured to be removably secured to an end effector 1122, which can include opposed jaws 1196 and/or a shroud 1150 that extends over a part of the jaws 1196. The cap 1120 can be in the form of a rigid, non-flexible housing having an inner lumen that can accept and capture the end effector 1122 therein. The cap 1120 can include structural features, such as one or more struts and walls, that surround at least a part of the inner lumen for protecting at least the jaws 1196 when the cap 1120 is coupled to the end effector 1122.

As shown in FIGS. 15A and 15C, the illustrated cap 1120 includes a spring flange 1124 adjacent a proximal end of the cap 1120 and having a protrusion 1126 along an inner surface of the spring flange 1124 that is configured to releasably engage a detent 1128 formed on the end effector 1122 or shroud 1150. However, in some embodiments, the end effector 1122 can include the protrusion 1126 and the spring flange 1124 can include the detent 1128. The spring flange 1124 can have a length and width that allows the spring flange 1124 to flex away from the end effector 1122 as the end effector 1122 is inserted in the inner lumen of the cap 1120. The lumen can be sized and shaped such that the jaws 1196 can travel therealong during removal of the cap 1120 without the lumen contacting the jaws 1196. Additionally, the spring flange 1124 can spring towards the end effector 1122 and allow the protrusion 1126 to engage the detent 1128 in the end effector 1122 for securing the cap 1120 to the end effector 1122. The cap 1120 can be removed by either twisting or pulling on the cap 1120 relative to the end effector 1122 to thereby disengage the protrusion 1126 from the detent 1128.

The shape of the protrusion 1126 and/or detent 1128, as well as the flexibility of the spring flange 1124, can cause the engagement between the protrusion 1126 and detent 1128 to be sufficient enough to retain the cap 1120 on the end effector 1122 while also allowing a user to efficiently pull the cap 1120 off the end effector 1122. For example, in some embodiments, the protrusion 1126 and detent 1128 can each have a circular or spherical shape, however, the protrusion 1126 and detent 1128 can have any number of shapes and sizes. Furthermore, any number of coupling features, such as the protrusion 1126 and detent 1128, can be positioned on end effector 1122 or the cap 1120. In some embodiments, as shown in FIG. 15B, the shroud 1150 can include the detent 1128 positioned along the longitudinal axis of a shaft 1118 to which the end effector 1122 is coupled to a distal end thereof. This positioning of the detent 1128 can allow the detent 1128 to be used as an alignment feature, such as during assembly and manufacturing (e.g., welding, inspection process, etc.).

The cap 1120 can include various other features that can assist with securing and/or removing the cap 1120 from the end effector 1122 of the clip applier. For example, the cap 1120 can include gripping features, such as ridges 1129, that can assist with allowing the user to efficiently and effectively grasp the cap 1120 and decouple the cap 1120 from the distal end of the clip applier. In some embodiments, the cap 1120 can include gripping features or ridges 1129 positioned transverse to a longitudinal axis of the cap 1120 and/or can include more than one gripping features or ridges 1129 positioned along opposing sides of the cap 1120, as shown in FIG. 15C. Furthermore, the cap 1120 can be made out of one or more of a variety of materials, such as one or more rigid materials including polymers (e.g., polycarbonate) and metals, as well as semi-rigid materials including elastomers, papers, woven fabrics, non-woven fabrics, and composite materials (e.g., made up of a combinations of two or more of the aforementioned materials). In some embodiments, the cap 1120 can be made out of an engineered plastic, such as Vectra, Ultem, or a nylon. Other features and variations of the cap 1120 are within the scope of this disclosure, including a cap 1120 that includes one or more indicators, e.g., an arrow 1130, for assisting with directing a user how to use the cap 1120, such as remove the cap 1120 from the distal end of the clip applier.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Reconditioning a device can utilize a variety of techniques for disassembly, cleaning/replacement, and reassembly. Use of such techniques, and the resulting reconditioned device, are all within the scope of the present application.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta, Gamma, or other forms of radiation, ethylene oxide, steam, or a liquid bath (e.g., cold soak). Certain forms of sterilization may be better suited to use with different portions of the device due to the materials utilized, the presence of electrical components, etc.

Furthermore, the teachings provided herein can also be applied to surgical methods for use of the above-described devices and/or creation of tissue seals and/or welds. For example, an exemplary method according to the teachings provided herein can include moving opposed jaw members of a surgical instrument end effector from an open position to a closed position to clamp tissue therebetween, applying compressive force to the clamped tissue using a closure mechanism that acts on a proximal end of the jaw members, and delivering energy through the clamped tissue to create a seal and/or weld. Increased stiffness of the opposed jaw members can result in better tissue grasping and improved compression, which can create a better quality tissue seal. In other embodiments, methods might also include inserting a surgical instrument into a patient's body while the jaw members are in an insertion configuration, and moving the end effector jaw members to a deployed configuration before clamping tissue. Still other variations are possible based on the teachings provided herein, all of which are considered within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical clip applier, comprising:
   an elongate shaft;
   a jaw insert having a proximal portion disposed within the elongate shaft and extending in a first plane containing a longitudinal axis of the shaft, and a distal portion having opposed first and second jaws extending in a second plane transverse to the first plane, the first and second jaws having opposed inner surfaces defining a clip track therebetween for receiving a distal-most clip from a plurality of clips disposed within the shaft;
   a former member disposed around the jaw insert and movable distally to cause the first and second jaws to move from an open position to a closed position to deform a clip seated in the clip track; and
   a shroud assembly disposed around the first and second jaws, the shroud assembly forming a gap relative thereto, wherein the gap limits movement of the first and second jaws along a single plane,
   wherein the opposed inner surfaces of the first and second jaws extend non-parallel to one another when the jaws are in the open position and extend substantially parallel to one another when the jaws are in the closed position.

2. The surgical clip applier of claim 1, wherein the shroud assembly comprises at least one mechanical interlock that is configured to fix a height of the gap.

3. The surgical clip applier of claim 2, wherein a first mechanical interlock of the at least one mechanical interlock comprises at least one of a keyed sliding-fit coupling, a stepped sliding-fit coupling, and a snap-fit coupling.

4. The surgical clip applier of claim 3, wherein a second mechanical interlock of the at least one mechanical interlock comprises a welded coupling.

5. The surgical clip applier of claim 2, wherein the at least one mechanical interlock comprises a first mechanical interlock comprising a hooked coupling and a second mechanical interlock comprising a spring flange coupling.

6. A surgical clip applier, comprising:
   a housing;
   a shaft extending from the housing;
   first and second jaws formed on a distal end of the shaft, the first and second jaws defining a clip track therebetween for receiving a distal-most clip from a plurality of clips disposed within the shaft;
   a former tube extending along the shaft and movable distally to move the first and second jaws from an open position to a closed position to deform a clip disposed in the clip track, the former tube having a coupling feature at a proximal end thereof; and
   a former plate disposed within the housing and having a u-shaped hook on a distal end positioned on one side of and in engagement with a flange on a proximal end of the coupling feature such that distal movement of the former plate causes corresponding distal movement of the former tube while allowing rotation of the shaft and the former tube relative to the housing and the former plate.

7. The surgical clip applier of claim 6, further comprising a shroud assembly that is disposed around the first and second jaws and that forms a gap relative thereto, wherein the gap limits movement of the first and second jaws along a single plane.

8. The surgical clip applier of claim 7, wherein the shroud assembly comprises at least one mechanical interlock that is configured to fix a height of the gap.

9. The surgical clip applier of claim 8, wherein a first mechanical interlock of the at least mechanical interlock comprises at least one of a keyed sliding-fit coupling, a stepped sliding-fit coupling, and a snap-fit coupling.

10. The surgical clip applier of claim 9, wherein the second mechanical interlock comprises a welded coupling.

11. The surgical clip applier of claim 8, wherein the at least one mechanical interlock comprises a first mechanical interlock comprising a hooked coupling and a second mechanical interlock comprising a spring flange coupling.

* * * * *